(12) United States Patent
Giroud et al.

(10) Patent No.: US 10,377,719 B2
(45) Date of Patent: Aug. 13, 2019

(54) TRYPANOSOMES INHIBITORS

(71) Applicant: Hoffmann-La Roche Inc., Little Falls, NJ (US)

(72) Inventors: Maude Giroud, Zurich (CH); Wolfgang Haap, Basel (CH); Bernd Kuhn, Basel (CH); Rainer E. Martin, Basel (CH)

(73) Assignee: Hoffmann-La Roche Inc., Little Falls (GB)

( * ) Notice: Subject to any disclaimer, the term of this patent is extended or adjusted under 35 U.S.C. 154(b) by 0 days.

(21) Appl. No.: 15/945,429

(22) Filed: Apr. 4, 2018

(65) Prior Publication Data

US 2018/0222866 A1   Aug. 9, 2018

Related U.S. Application Data

(63) Continuation of application No. PCT/EP2016/078539, filed on Nov. 23, 2016.

(30) Foreign Application Priority Data

Nov. 26, 2015 (EP) ..................... 15196575

(51) Int. Cl.
| | | |
|---|---|---|
| *A61P 33/02* | (2006.01) | |
| *A61K 31/415* | (2006.01) | |
| *A61K 31/4155* | (2006.01) | |
| *A61K 31/421* | (2006.01) | |
| *A61K 31/4192* | (2006.01) | |
| *A61K 31/42* | (2006.01) | |
| *A61K 31/422* | (2006.01) | |
| *A61K 31/4245* | (2006.01) | |
| *A61K 31/443* | (2006.01) | |
| *A61K 31/4439* | (2006.01) | |
| *C07D 231/14* | (2006.01) | |
| *C07D 263/34* | (2006.01) | |
| *C07D 405/02* | (2006.01) | |
| *C07D 249/06* | (2006.01) | |
| *C07D 401/04* | (2006.01) | |
| *C07D 403/02* | (2006.01) | |
| *C07D 261/18* | (2006.01) | |
| *C07D 271/06* | (2006.01) | |
| *C07D 271/10* | (2006.01) | |
| *C07D 401/12* | (2006.01) | |
| *C07D 213/56* | (2006.01) | |
| *C07D 403/04* | (2006.01) | |
| *C07D 407/04* | (2006.01) | |
| *C07D 261/10* | (2006.01) | |
| *C07D 405/04* | (2006.01) | |

(52) U.S. Cl.
CPC ............ *C07D 231/14* (2013.01); *A61P 33/02* (2018.01); *C07D 213/56* (2013.01); *C07D 249/06* (2013.01); *C07D 261/10* (2013.01); *C07D 261/18* (2013.01); *C07D 263/34* (2013.01); *C07D 271/06* (2013.01); *C07D 271/10* (2013.01); *C07D 401/04* (2013.01); *C07D 401/12* (2013.01); *C07D 403/04* (2013.01); *C07D 405/04* (2013.01); *C07D 407/04* (2013.01)

(58) Field of Classification Search
CPC ... A61P 33/02; A61K 31/415; A61K 31/4155; A61K 31/421; A61K 31/4192; A61K 31/3142; A61K 31/422; A61K 31/4245; A61K 31/443; A61K 31/4439; A61K 31/42; C07D 231/14; C07D 263/34; C07D 405/02; C07D 249/06; C07D 401/04; C07D 403/02; C07D 261/18; C07D 271/06; C07D 271/10; C07D 401/12; C07D 213/56
See application file for complete search history.

(56) References Cited

U.S. PATENT DOCUMENTS 6,353,017 B1   5/2002   Altmann et al.

FOREIGN PATENT DOCUMENTS

| WO | 2007/012180 A1 | 2/2007 |
|---|---|---|
| WO | 2010/148488 A1 | 12/2010 |

OTHER PUBLICATIONS

ISR for PCT/EP2016/078539 (dated Mar. 7, 2017).

*Primary Examiner* — Brenda L Coleman
(74) *Attorney, Agent, or Firm* — Brian L. Buckwalter

(57) ABSTRACT

The invention relates to a compound of formula (I)

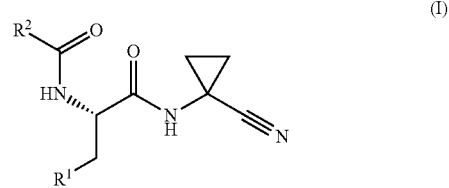

(I)

wherein $R^1$ and $R^2$ are defined as in the description and in the claims. The compound of formula (I) can be used as a medicament.

28 Claims, No Drawings

TRYPANOSOMES INHIBITORS

CROSS REFERENCE TO RELATED APPLICATIONS

This application is a continuation of International Application No. PCT/EP2016/078539 having an international filing date of Nov. 23, 2016 and which claims benefit under 35 U.S.C. § 119 European Patent Application 15196575.3 having an international filing date of Nov. 26, 2015. The entire contents of both are incorporated herein by reference.

FIELD OF THE INVENTION

The present invention relates to compounds of formula I that are trypanosome inhibitors, their manufacture, pharmaceutical compositions containing them and their potential use as medicaments. The compounds of formula I may be used for the treatment and of Human African Trypanosomiasis.

BACKGOUND OF THE INVENTION

Human African Trypanosomiasis (HAT) or African Sleeping Sickness is caused by protozoan parasites belonging to the genus *Trypanosoma*. These parasites are transmitted to humans by tsetse fly (*Glossina* genus) bites which have acquired their infection from human beings or from animals harbouring the human pathogenic parasites. There are two different parasites known to cause the disease: *Trypanosoma brucei* gambiense and *Trypanosoma brucei* rhodesiense. Humans once infected with the parasite undergo two different stages of the disease. In the first stage, the trypanosomes multiply in subcutaneous tissues, blood and lymph. This is also called haemo-lymphatic stage, which entails bouts of fever, headaches, joint pains and itching. In the second stage the parasites cross the blood-brain barrier to infect the central nervous system (CNS). This is known as the neurological or meningo-encephalic stage. In general this is when more obvious signs and symptoms of the disease appear: changes of behaviour, confusion, sensory disturbances and poor coordination. Disturbance of the sleep cycle, which gives the disease its name, is an important feature. Without treatment, sleeping sickness is considered fatal although cases of healthy carriers have been reported.

Current treatment regimen include for stage one disease Pentamidine and Suramin. For stage two disease with manifested CNS infections several treatment options are available. Melarsoprol, an arsene containing compound, Eflornithine and Nifurtimox and especially the combination of the latter two compounds are the current first-line treatment options particularly for the gambiense form of HAT (Trypanosomiasis, human African sleeping sickness; WHO; Fact sheet No 259; http://www.who.int/mediacentre/factsheets/fs259/en/).

All these drugs are not completely satisfactory, due to poor efficacy, undesirable route of administration, drug resistance and undesirable side effects. Toxicity is also a major problem, for example, Melarsoprol have associated 5% death due to the side effects. In November 2013, the WHO Expert Committee argued that, despite the advancements in HAT treatment, all currently available options are suboptimal, and the development of new, safe compounds that are effective against both disease stages and are easy to use is a high priority (Stella Peña, Laura Scarone & Gloria Serra, Future Medicinal Chemistry, Vol. 7, No. 3, Pages 355-382 (2015)).

SUMMARY OF THE INVENTION

The present invention relates to compounds of formula (I)

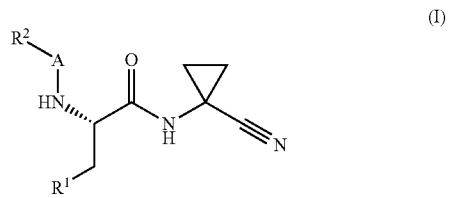

(I)

wherein

A is —C(O)— or —CHCF$_3$—;

R$^1$ is propyl, pyridinyl or R$^3$;

R$^2$ is (A), (B), (C), (D), (E), (F) or (G);

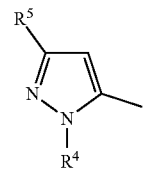

(A)

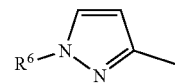

(B)

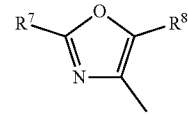

(C)

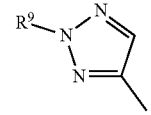

(D)

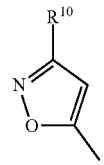

(E)

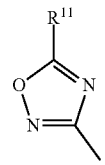

(F)

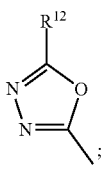

(G)

$R^3$ is (H);

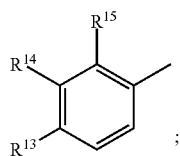

(H)

$R^4$ is hydrogen, alkyl or haloalkyl;
$R^5$ is alkyl, haloalkyl, cycloalkyl, phenyl, halophenyl or alkoxyphenyl;
$R^6$ is halophenyl;
$R^7$ is halophenyl;
$R^8$ is alkyl;
$R^9$ is alkyl, cycloalkyl, halocycloalkyl, phenyl, halophenyl, alkylsulphanylphenyl, pyridinyl, halopyridinyl, oxanyl, azaspiro[3.3]heptyl, alkoxycarbonylazaspiro[3.3]heptyl, oxetanyl, pyrrolidinyl, alkoxycarbonylpyrrolidinyl, azetidinyl or alkylcarbonylazetidinyl;
$R^{10}$ is phenyl;
$R^{11}$ is halophenyl;
$R^{12}$ is phenyl or halophenyl;
$R^{13}$ is hydrogen, halogen, haloalkyl, haloalkoxy, cycloalkylalkoxy, phenylalkoxy, alkoxyalkoxy or cyano;
$R^{14}$ is hydrogen, halogen or haloalkyl; and
$R^{15}$ is hydrogen, halogen, cyano or haloalkyl;
or a pharmaceutically acceptable salt or ester thereof;
provided that N-[(1S)-1-[(3-chlorophenyl)methyl]-2-[(1-cyanocyclopropyl)amino]-2-oxoethyl]-3-(1,1-dimethylethyl)-1-methyl-1H-pyrazole-5-carboxamide is excluded.

DETAILED DESCRIPTION OF THE INVENTION

The present invention provides novel compounds that offer effective treatment options for HAT.

In the present description the term "alkyl", alone or in combination, signifies a straight-chain or branched-chain alkyl group with 1 to 8 carbon atoms, particularly a straight or branched-chain alkyl group with 1 to 6 carbon atoms and more particularly a straight or branched-chain alkyl group with 1 to 4 carbon atoms. Examples of straight-chain and branched-chain $C_1$-$C_8$ alkyl groups are methyl, ethyl, propyl, isopropyl, butyl, isobutyl, tert.-butyl, the isomeric pentyls, the isomeric hexyls, the isomeric heptyls and the isomeric octyls, particularly methyl, ethyl, propyl, butyl and pentyl more particularly methyl, ethyl, propyl, isopropyl, isobutyl, tert.-butyl and isopentyl. Particular examples of alkyl are methyl, propyl and tert.-butyl.

The term "cycloalkyl", alone or in combination, signifies a cycloalkyl ring with 3 to 8 carbon atoms and particularly a cycloalkyl ring with 3 to 6 carbon atoms. Examples of cycloalkyl are cyclopropyl, cyclobutyl, cyclopentyl and cyclohexyl, cycloheptyl and cyclooctyl. Particular examples of "cycloalkyl" are cyclopropyl, cyclobutyl or cyclohexyl.

The term "alkoxy", alone or in combination, signifies a group of the formula alkyl-O— in which the term "alkyl" has the previously given significance, such as methoxy, ethoxy, n-propoxy, isopropoxy, n-butoxy, isobutoxy, sec-butoxy and tert.-butoxy. Particular "alkoxy" are methoxy, ethoxy and tert.-butyloxy.

The term "oxy", alone or in combination, signifies the —O— group.

The terms "halogen" or "halo", alone or in combination, signifies fluorine, chlorine, bromine or iodine and particularly fluorine, chlorine or bromine. The term "halo", in combination with another group, denotes the substitution of said group with at least one halogen, particularly substituted with one to five halogens, particularly one to four halogens, i.e. one, two, three or four halogens.

The term "haloalkyl", alone or in combination, denotes an alkyl group substituted with at least one halogen, particularly substituted with one to five halogens, particularly one to three halogens. A particular "haloalkyl" is trifluoromethyl.

The term "haloalkoxy", alone or in combination, denotes an alkoxy group substituted with at least one halogen, particularly substituted with one to five halogens, particularly one to three halogens. A particular "haloalkoxy" is trifluoromethoxy.

The term "carbonyl", alone or in combination, signifies the —C(O)— group.

The term "sulfanyl", alone or in combination, signifies the —S— group.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid, particularly hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein. In addition these salts may be prepared form addition of an inorganic base or an organic base to the free acid. Salts derived from an inorganic base include, but are not limited to, the sodium, potassium, lithium, ammonium, calcium, magnesium salts. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins. The compound of formula (I) can also be present in the form of zwitterions. Particularly preferred pharmaceutically acceptable salts of compounds of formula (I) are the salts of hydrochloric acid, hydrobromic acid, sulfuric acid, phosphoric acid and methanesulfonic acid.

"Pharmaceutically acceptable esters" means that the compound of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compound of general formula (I), similar to the metabolically labile esters, which are capable of producing the parent compound of general formula (I) in vivo, are within the scope of this invention.

If one of the starting materials or compounds of formula (I) contain one or more functional groups which are not stable or are reactive under the reaction conditions of one or more reaction steps, appropriate protecting groups (as described e.g. in "Protective Groups in Organic Chemistry" by T. W. Greene and P. G. M. Wuts, 3$^{rd}$ Ed., 1999, Wiley, New York) can be introduced before the critical step applying methods well known in the art. Such protecting groups can be removed at a later stage of the synthesis using standard methods described in the literature. Examples of protecting groups are tert-butoxycarbonyl (Boc), 9-fluorenylmethyl carbamate (Fmoc), 2-trimethylsilylethyl carbamate (Teoc), carbobenzyloxy (Cbz) and p-methoxybenzyloxycarbonyl (Moz).

The compound of formula (I) can contain several asymmetric centers and can be present in the form of optically pure enantiomers, mixtures of enantiomers such as, for example, racemates, mixtures of diastereoisomers, diastereoisomeric racemates or mixtures of diastereoisomeric racemates.

The term "asymmetric carbon atom" means a carbon atom with four different substituents. According to the Cahn-Ingold-Prelog Convention an asymmetric carbon atom can be of the "R" or "S" configuration.

The invention thus relates in particular to

A compound of formula (I) wherein A is —C(O)—;
A compound of formula (I) wherein $R^1$ is $R^3$;
A compound of formula (I) wherein $R^2$ is (D) or (E);
A compound of formula (I) wherein $R^4$ is hydrogen, methyl or difluoroethyl;
A compound of formula (I) wherein $R^5$ is methyl, tert.-butyl, trifluoromethyl, cyclopropyl, phenyl, chlorophenyl, fluorophenyl or methoxyphenyl;
A compound of formula (I) wherein $R^6$ is fluorophenyl;
A compound of formula (I) wherein $R^7$ is chlorophenyl;
A compound of formula (I) wherein $R^8$ is methyl;
A compound of formula (I) wherein $R^9$ is alkyl, phenyl, halophenyl, pyridinyl or halopyridinyl;
A compound of formula (I) wherein $R^9$ is methyl, propyl, tert.-butyl, phenyl, fluorophenyl, chlorophenyl, pyridinyl or fluoropyridinyl;
A compound of formula (I) wherein $R^{11}$ is chlorophenyl or fluorophenyl;
A compound of formula (I) wherein $R^{12}$ is phenyl or bromophenyl;
A compound of formula (I) wherein $R^{13}$ is halogen, haloalkoxy or alkoxyalkoxy;
A compound of formula (I) wherein $R^{13}$ is chloro, trifluoromethoxy or methoxyethoxy;
A compound of formula (I) wherein $R^{14}$ is halogen;
A compound of formula (I) wherein $R^{14}$ is chloro; and
A compound of formula (I) wherein $R^{15}$ is hydrogen.

The invention further relates to a compound of formula (I) selected from (S)—N-(3-(3-chloro-4-(trifluoromethoxy)phenyl)-1-(1-cyanocyclopropylamino)-1-oxopropan-2-yl)-1-(2,2-difluoroethyl)-3-(trifluoromethyl)-1H-pyrazole-5-carboxamide;

(S)—N-(3-(3-chloro-4-(trifluoromethoxy)phenyl)-1-(1-cyanocyclopropylamino)-1-oxopropan-2-yl)-1-methyl-3-(trifluoromethyl)-1H-pyrazole-5-carboxamide;

(S)—N-(3-(3-chloro-4-(trifluoromethoxy)phenyl)-1-(1-cyanocyclopropylamino)-1-oxopropan-2-yl)-1,3-dimethyl-1H-pyrazole-5-carboxamide;

(S)—N-(3-(3-chloro-4-(trifluoromethoxy)phenyl)-1-(1-cyanocyclopropylamino)-1-oxopropan-2-yl)-3-cyclopropyl-1-methyl-1H-pyrazole-5-carboxamide;

(S)-3-tert-butyl-N-(3-(3-chloro-4-(trifluoromethoxy)phenyl)-1-(1-cyanocyclopropylamino)-1-oxopropan-2-yl)-1-methyl-1H-pyrazole-5-carboxamide;

(S)—N-(3-(3-chloro-4-(trifluoromethoxy)phenyl)-1-(1-cyanocyclopropylamino)-1-oxopropan-2-yl)-1-(4-fluorophenyl)-1H-pyrazole-3-carboxamide;

(S)—N-(3-(3-chloro-4-(trifluoromethoxy)phenyl)-1-(1-cyanocyclopropylamino)-1-oxopropan-2-yl)-1-methyl-3-phenyl-1H-pyrazole-5-carboxamide;

(S)—N-(3-(3-chloro-4-(trifluoromethoxy)phenyl)-1-(1-cyanocyclopropylamino)-1-oxopropan-2-yl)-2-(4-chlorophenyl)-5-methyloxazole-4-carboxamide;

(S)—N-(3-(3-chloro-4-(trifluoromethoxy)phenyl)-1-(1-cyanocyclopropylamino)-1-oxopropan-2-yl)-2-(4-fluorophenyl)-2H-1,2,3-triazole-4-carboxamide;

(S)—N-(3-(3-chloro-4-(trifluoromethoxy)phenyl)-1-(1-cyanocyclopropylamino)-1-oxopropan-2-yl)-3-(2-chlorophenyl)-1H-pyrazole-5-carboxamide;

(S)—N-(3-(3-chloro-4-(trifluoromethoxy)phenyl)-1-(1-cyanocyclopropylamino)-1-oxopropan-2-yl)-3-(4-fluorophenyl)-1H-pyrazole-5-carboxamide;

(S)—N-(3-(3-chloro-4-(trifluoromethoxy)phenyl)-1-(1-cyanocyclopropylamino)-1-oxopropan-2-yl)-3-(4-methoxyphenyl)-1H-pyrazole-5-carboxamide, (S)—N-(3-(3-chloro-4-(trifluoromethoxy)phenyl)-1-(1-cyanocyclopropylamino)-1-oxopropan-2-yl)-3-phenylisoxazole-5-carboxamide;

(S)—N-(3-(3-chloro-4-(trifluoromethoxy)phenyl)-1-(1-cyanocyclopropylamino)-1-oxopropan-2-yl)-5-methyl-2-phenyl-2H-1,2,3-triazole-4-carboxamide;

(S)—N-(3-(3-chloro-4-(trifluoromethoxy)phenyl)-1-(1-cyanocyclopropylamino)-1-oxopropan-2-yl)-5-(3-fluorophenyl)-1,2,4-oxadiazole-3-carboxamide;

(S)—N-(3-(3-chloro-4-(trifluoromethoxy)phenyl)-1-(1-cyanocyclopropylamino)-1-oxopropan-2-yl)-2-phenyl-2H-1,2,3-triazole-4-carboxamide;

(S)—N-(3-(3-chloro-4-(trifluoromethoxy)phenyl)-1-(1-cyanocyclopropylamino)-1-oxopropan-2-yl)-3-(3-chlorophenyl)-1-methyl-1H-pyrazole-5-carboxamide;

(S)—N-(3-(3-chloro-4-(trifluoromethoxy)phenyl)-1-(1-cyanocyclopropylamino)-1-oxopropan-2-yl)-5-(3-chlorophenyl)-1,2,4-oxadiazole-3-carboxamide;

(2S)-2-[[1-[5-(4-bromophenyl)-1,3,4-oxadiazol-2-yl]-2,2,2-trifluoroethyl]amino]-3-[3-chloro-4-(trifluoromethoxy)phenyl]-N-(1-cyanocyclopropyl)propanamide;

(2S)-2-(1-(5-(4-bromophenyl)-1,3,4-oxadiazol-2-yl)-2,2,2-trifluoroethylamino)-3-(3-chloro-4-(trifluoromethoxy)phenyl)-N-(1-cyanocyclopropyl)propanamide;

(2S)-3-(3-chloro-4-(trifluoromethoxy)phenyl)-N-(1-cyanocyclopropyl)-2-(2,2,2-trifluoro-1-(5-phenyl-1,3,4-oxadiazol-2-yl)ethylamino)propanamide;

(2S)-3-(3-chloro-4-(trifluoromethoxy)phenyl)-N-(1-cyanocyclopropyl)-2-((2,2,2-trifluoro-1-(5-phenyl-1,3,4-oxadiazol-2-yl)ethyl)amino)propanamide;

N-[(2S)-3-[3-chloro-4-(trifluoromethoxy)phenyl]-1-[(1-cyanocyclopropyl)amino]-1-oxopropan-2-yl]-2-(4-methylsulfanylphenyl)triazole-4-carboxamide;

2-(4-chlorophenyl)-N-[(2S)-3-[3-chloro-4-(trifluoromethoxy)phenyl]-1-[(1-cyanocyclopropyl)amino]-1-oxopropan-2-yl]triazole-4-carboxamide;

N-[(2S)-3-(3-chlorophenyl)-1-[(1-cyanocyclopropyl)amino]-1-oxopropan-2-yl]-2-(4-fluorophenyl)triazole-4-carboxamide;

N-[(2S)-3-[3-chloro-4-(trifluoromethoxy)phenyl]-1-[(1-cyanocyclopropyl)amino]-1-oxopropan-2-yl]-2-pyridin-3-yltriazole-4-carboxamide;

N-[(2S)-1-[(1-cyanocyclopropyl)amino]-1-oxo-3-phenylpropan-2-yl]-2-(4-fluorophenyl)triazole-4-carboxamide;

N-[(2S)-3-[3-chloro-4-(cyclopropylmethoxy)phenyl]-1-[(1-cyanocyclopropyl)amino]-1-oxopropan-2-yl]-2-(4-fluorophenyl)triazole-4-carboxamide;

N-[(2S)-1-[(1-cyanocyclopropyl)amino]-3-(3,4-dichlorophenyl)-1-oxopropan-2-yl]-2-(4-fluorophenyl)triazole-4-carboxamide;

N-[(2S)-3-[3-chloro-4-(trifluoromethoxy)phenyl]-1-[(1-cyanocyclopropyl)amino]-1-oxopropan-2-yl]-2-(6-fluoropyridin-3-yl)triazole-4-carboxamide;

N-[(2S)-1-[(1-cyanocyclopropyl)amino]-1-oxo-3-(4-phenylmethoxyphenyl)propan-2-yl]-2-(4-fluorophenyl)triazole-4-carboxamide;

N-[(2S)-1-[(1-cyanocyclopropyl)amino]-4-methyl-1-oxopentan-2-yl]-2-(4-fluorophenyl)triazole-4-carboxamide;

N-[(2S)-3-[3-chloro-4-(trifluoromethoxy)phenyl]-1-[(1-cyanocyclopropyl)amino]-1-oxopropan-2-yl]-2-propan-2-yltriazole-4-carboxamide;

N-[(2S)-3-[3-chloro-4-(trifluoromethoxy)phenyl]-1-[(1-cyanocyclopropyl)amino]-1-oxopropan-2-yl]-2-methyltriazole-4-carboxamide;

2-(4-bromophenyl)-N-[(2S)-3-[3-chloro-4-(trifluoromethoxy)phenyl]-1-[(1-cyanocyclopropyl)amino]-1-oxopropan-2-yl]triazole-4-carboxamide;

N-[(2S)-3-[3-chloro-4-(2-methoxyethoxy)phenyl]-1-[(1-cyanocyclopropyl)amino]-1-oxopropan-2-yl]-2-(4-fluorophenyl)triazole-4-carboxamide;

2-tert-butyl-N-[(2S)-3-[3-chloro-4-(trifluoromethoxy)phenyl]-1-[(1-cyanocyclopropyl)amino]-1-oxopropan-2-yl]triazole-4-carboxamide;

N-[(2S)-3-[3-chloro-4-(cyclobutylmethoxy)phenyl]-1-[(1-cyanocyclopropyl)amino]-1-oxopropan-2-yl]-2-(4-fluorophenyl)triazole-4-carboxamide;

N-[(2S)-1-[(1-cyanocyclopropyl)amino]-1-oxo-3-pyridin-4-ylpropan-2-yl]-2-(4-fluorophenyl)triazole-4-carboxamide;

N-[(2S)-3-(4-chlorophenyl)-1-[(1-cyanocyclopropyl)amino]-1-oxopropan-2-yl]-2-(4-fluorophenyl)triazole-4-carboxamide;

N-[(2S)-3-[3-chloro-4-(trifluoromethoxy)phenyl]-1-[(1-cyanocyclopropyl)amino]-1-oxopropan-2-yl]-2-pyridin-4-yltriazole-4-carboxamide;

N-[(2S)-3-[3-chloro-4-(trifluoromethoxy)phenyl]-1-[(1-cyanocyclopropyl)amino]-1-oxopropan-2-yl]-2-cyclobutyltriazole-4-carboxamide;

N-[(2S)-3-(3-chloro-4-cyanophenyl)-1-[(1-cyanocyclopropyl)amino]-1-oxopropan-2-yl]-2-(4-fluorophenyl)triazole-4-carboxamide;

N-[(2S)-3-[3-chloro-4-(trifluoromethoxy)phenyl]-1-[(1-cyanocyclopropyl)amino]-1-oxopropan-2-yl]-2-(oxan-4-yl)triazole-4-carboxamide;

N-[(2S)-1-[(1-cyanocyclopropyl)amino]-3-(3,4-dichlorophenyl)-1-oxopropan-2-yl]-2-(oxan-4-yl)triazole-4-carboxamide;

N-[(2S)-3-[3-chloro-4-(trifluoromethoxy)phenyl]-1-[(1-cyanocyclopropyl)amino]-1-oxopropan-2-yl]-2-cyclohexyltriazole-4-carboxamide;

N-[(2S)-1-[(1-cyanocyclopropyl)amino]-3-(2-cyanophenyl)-1-oxopropan-2-yl]-2-(4-fluorophenyl)triazole-4-carboxamide;

N-[(2S)-1-[(1-cyanocyclopropyl)amino]-1-oxo-3-[2-(trifluoromethyl)phenyl]propan-2-yl]-2-(4-fluorophenyl)triazole-4-carboxamide;

N-[(2S)-3-(2-chlorophenyl)-1-[(1-cyanocyclopropyl)amino]-1-oxopropan-2-yl]-2-(4-fluorophenyl)triazole-4-carboxamide;

N-[(2S)-1-[(1-cyanocyclopropyl)amino]-3-(3,4-dichlorophenyl)-1-oxopropan-2-yl]-2-(3,3-difluorocyclobutyl)triazole-4-carboxamide;

tert-butyl 6-[4-[[(2S)-3-[3-chloro-4-(trifluoromethoxy)phenyl]-1-[(1-cyanocyclopropyl)amino]-1-oxopropan-2-yl]carbamoyl]triazol-2-yl]-2-azaspiro[3.3]heptane-2-carboxylate;

N-[(2S)-1-[(1-cyanocyclopropyl)amino]-3-(3,4-dichlorophenyl)-1-oxopropan-2-yl]-2-cyclobutyltriazole-4-carboxamide;

N-[(2S)-3-[3-chloro-4-(trifluoromethoxy)phenyl]-1-[(1-cyanocyclopropyl)amino]-1-oxopropan-2-yl]-2-(3,3-difluorocyclobutyl)triazole-4-carboxamide;

N-[(2S)-1-[(1-cyanocyclopropyl)amino]-3-(3,4-dichlorophenyl)-1-oxopropan-2-yl]-2-(oxetan-3-yl)triazole-4-carboxamide;

N-[(2S)-3-[3-chloro-4-(trifluoromethoxy)phenyl]-1-[(1-cyanocyclopropyl)amino]-1-oxopropan-2-yl]-2-(oxetan-3-yl)triazole-4-carboxamide;

2-(2-azaspiro[3.3]heptan-6-yl)-N-[(2S)-3-[3-chloro-4-(trifluoromethoxy)phenyl]-1-[(1-cyanocyclopropyl)amino]-1-oxopropan-2-yl]triazole-4-carboxamide;

tert-butyl 3-[4-[[(2S)-3-[3-chloro-4-(trifluoromethoxy)phenyl]-1-[(1-cyanocyclopropyl)amino]-1-oxopropan-2-yl]carbamoyl]triazol-2-yl]pyrrolidine-1-carboxylate;

N-[(2S)-3-[3-chloro-4-(trifluoromethoxy)phenyl]-1-[(1-cyanocyclopropyl)amino]-1-oxopropan-2-yl]-2-pyrrolidin-3-yltriazole-4-carboxamide;

2-(azetidin-3-yl)-N-[(2S)-3-[3-chloro-4-(trifluoromethoxy)phenyl]-1-[(1-cyanocyclopropyl)amino]-1-oxopropan-2-yl]triazole-4-carboxamide; and N-[(2S)-1-[(1-cyanocyclopropyl)amino]-1-oxo-3-pyridin-2-ylpropan-2-yl]-2-(4-fluorophenyl)triazole-4-carboxamide.

The invention also relates to a compound of formula (I) selected from (S)—N-(3-(3-chloro-4-(trifluoromethoxy)phenyl)-1-(1-cyanocyclopropylamino)-1-oxopropan-2-yl)-2-(4-fluorophenyl)-2H-1,2,3-triazole-4-carboxamide;

(S)—N-(3-(3-chloro-4-(trifluoromethoxy)phenyl)-1-(1-cyanocyclopropylamino)-1-oxopropan-2-yl)-3-phenylisoxazole-5-carboxamide;

(S)—N-(3-(3-chloro-4-(trifluoromethoxy)phenyl)-1-(1-cyanocyclopropylamino)-1-oxopropan-2-yl)-2-phenyl-2H-1,2,3-triazole-4-carboxamide;

2-(4-chlorophenyl)-N-[(2S)-3-[3-chloro-4-(trifluoromethoxy)phenyl]-1-[(1-cyanocyclopropyl)amino]-1-oxopropan-2-yl]triazole-4-carboxamide;

N-[(2S)-3-[3-chloro-4-(trifluoromethoxy)phenyl]-1-[(1-cyanocyclopropyl)amino]-1-oxopropan-2-yl]-2-pyridin-3-yltriazole-4-carboxamide;

N-[(2S)-1-[(1-cyanocyclopropyl)amino]-3-(3,4-dichlorophenyl)-1-oxopropan-2-yl]-2-(4-fluorophenyl)triazole-4-carboxamide;

N-[(2S)-3-[3-chloro-4-(trifluoromethoxy)phenyl]-1-[(1-cyanocyclopropyl)amino]-1-oxopropan-2-yl]-2-(6-fluoropyridin-3-yl)triazole-4-carboxamide;

N-[(2S)-3-[3-chloro-4-(trifluoromethoxy)phenyl]-1-[(1-cyanocyclopropyl)amino]-1-oxopropan-2-yl]-2-propan-2-yltriazole-4-carboxamide;

N-[(2S)-3-[3-chloro-4-(trifluoromethoxy)phenyl]-1-[(1-cyanocyclopropyl)amino]-1-oxopropan-2-yl]-2-methyltriazole-4-carboxamide;

N-[(2S)-3-[3-chloro-4-(2-methoxyethoxy)phenyl]-1-[(1-cyanocyclopropyl)amino]-1-oxopropan-2-yl]-2-(4-fluorophenyl)triazole-4-carboxamide; and 2-tert-butyl-N-[(2S)-3-[3-chloro-4-(trifluoromethoxy)phenyl]-1-[(1-cyanocyclopropyl)amino]-1-oxopropan-2-yl]triazole-4-carboxamide.

The compound of formula (I) can be manufactured according to the following procedures.

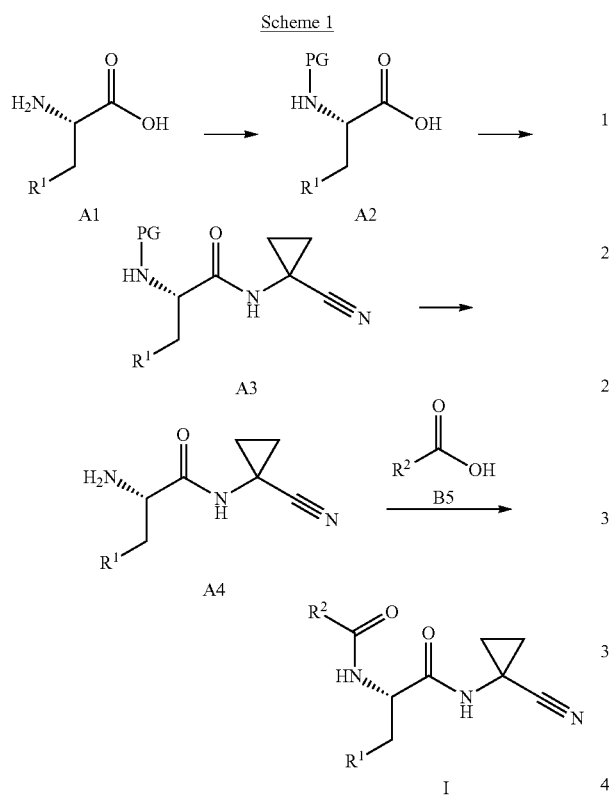

Non-commercially available L-aminoacids of general formula A2 can be obtained upon protection of the amine functionality. When protecting group (PG)=Boc, compound A2 was obtained upon treatment of A1 with di-tert-butyl dicarbonate and a base such as NaOH or iPr₂NEt in solvents such as 1,4-dioxane or CH₂Cl₂, more particularly NaOH in 1:1 1,4-dioxane/H₂O. When PG=Fmoc, commercially available L-amino acids of general formula A1 were treated with fluorenylmethyloxycarbonyl chloride and a base, such as iPr₂NEt, to afford intermediate A2.

Compounds of general formula A2 comprise commercially available protected L-amino acids, where PG=Boc or PG=Fmoc or L-amino acids prepared from compounds A1 as above-mentioned.

Compounds of general formula A3 can be prepared from intermediate A2. Typically, treatment of intermediate A2 with an amine, most particularly 1-aminocyclopropanecarbonitrile hydrochloride, a coupling agent such as e.g. 1-[bis(dimethylamino)methylene]-1H-1,2,3-triazolo[4,5-b]pyridinium 3-oxide hexafluorophosphate (HATU), 3-[bis(dimethylamino)methyliumyl]-3H-benzotriazol-1-oxide hexafluorophosphate (HBTU), or 3-(ethyliminomethyleneamino)-N,N-dimethylpropan-1-amine (EDCI), most particularly HATU, in the presence of a non-nucleophilic base such as iPr₂NEt in a polar aprotic solvent such as dimethylformamide (DMF) or dimethylacetamide (DMA), most particularly DMF, at 0° C. or 22° C., preferably at 0° C.

Amines of general formula A4 can be prepared via deprotection of compounds A3. When PG=Boc, the carbamate can be typically cleaved with an acid such as trifluoroacetic acid (TFA) or HCl, most particularly formic acid, at 22° C. When PG=Fmoc, the carbamate is typically cleaved with piperidine in CH₂Cl₂, at 22° C.

Compounds of general formula (I) was be prepared from intermediates A4 and B5 in an amide coupling. Typically, treatment of intermediate A4 with a carboxylic acid of general formula B5 with a coupling agent such as e.g. HATU, HBTU, or EDCI, most particularly HATU, in the presence of a non-nucleophilic base such as iPr₂NEt in a polar aprotic solvent such as DMF or DMA, most particularly DMF, at 0° C. or 22° C., preferably at 0° C., afforded compounds I.

The intermediate of general formula B5 is either commercially available or can be prepared as described in Scheme 2.

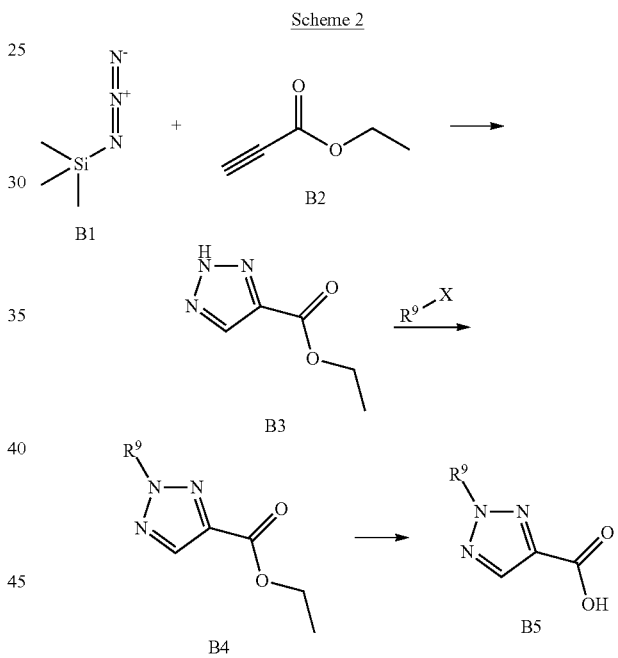

Triazole B3 can be prepared by 1,3-dipolar cycloaddition of trimethylsilyl azide (B1) with ethyl propiolate (B2). Previous report (*J. Heterocyclic Chem.* 2009, 46, 131) run the reaction neat under MW irradiation (60 W, 10 min), affording triazole B3 in 83% yield. However due to safety related considerations and limited scalability of this procedure, we developed a flow synthesis of the triazole B3. Using acetonitrile as system solvent and injecting both commercially available starting materials neat and processing at 140° C. for 30 min, the desired triazole was afforded in 81% yield, as a white solid. This process has a productivity of 8.7 g/h.

Derivatization of the Intermediate B3 was Performed Following Five Different Procedures:

When X=Br, a Buchwald-Hartwig coupling was performed, as reported by Satoshi Ueda, Mingjuan Su, and Stephen Buchwald in *Ang. Chem. Int. Ed.* 2011, 50, 8944-8947.

When X=B(OH)$_2$, a Chan-Lam coupling was performed, using pyridine or KOtBu as a base, Cu(OAc)$_2$ as copper source, and DMF or DMA, preferably DMA, as solvent.

When X=I and R$^9$=Methyl or Isopropyl, a substitution was performed, using K$_2$CO$_3$ as base, and acetonitrile as solvent.

When X=OH and R$^9$=tert-butyl, the mixture was treated with trifluoroacetic acid (TFA) and sulfuric acid, at 22° C.

When X=OH and R$^9$=cyclobutyl, oxetanyl, or any other saturated compound other than methyl, isopropyl, and tert-butyl, intermediate B4 could be obtained via a Mitsunobu reaction, using e.g. diethyl diazenedicarboxylate (DEAD) and triphenyl phosphine, more particularly 2-(tributylphosphoranylidene)acetonitrile in toluene, at 80° C.

Intermediate B5 was obtained by saponification of intermediate B6, using typically a base such as NaOH or LiOH, more particularly LiOH, in 2:2:1 THF/MeOH/H$_2$O, at 22° C.

When R$^9$=tert-butyl 6-hydroxy-2-azaspiro[3.3]heptane-2-carboxylate, tert-butyl 3-hydroxypyrrolidine-1-carboxylate or tert-butyl 2-azetidine-3-yl, compound A4 was treated with formic acid at 22° C., affording amines of general formula I.

In Scheme 3, the synthesis of compounds of general formula (I) with R$^1$=2-chloro-4-methylphenol is described.

Scheme 3

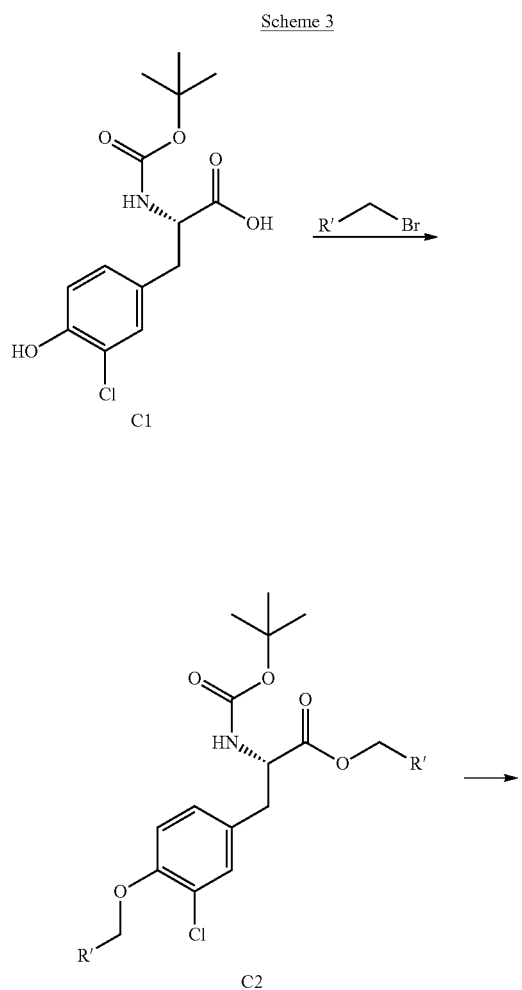

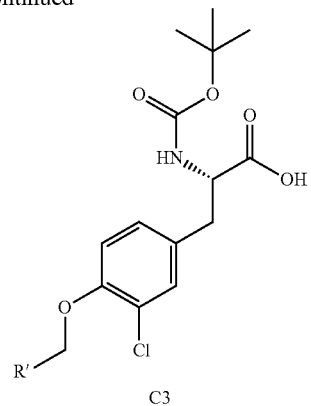

R' is phenyl, cycloalkyl (e.g. cyclopropyl, cyclobutyl) or methoxymethyl.

Intermediate C2 can be prepared from commercially available tyrosine derivatives C1 and an alkyl bromide of general formula R'CH2Br with an inorganic base such as K$_2$CO$_3$ or Cs$_2$CO$_3$, generally Cs$_2$CO$_3$, in a polar aprotic solvent, e.g. DMA, DMF, or ACN, preferably DMF, affording intermediates C2.

Carboxylic acid of general formula C3 can be obtained upon saponification of intermediate C2 using a base such as NaOH or LiOH, preferably LiOH, in 2:2:1 THF/MeOH/H$_2$O. Carboxylic acids of general formula C3 can also be defined as intermediate A2, with PG=Boc and R$^1$=2-chloro-1-(R'-methoxy)-4-methyl-benzene). From intermediate C3 on, the synthesis follows the route of Scheme 1, from general formula A2.

Scheme 4 Describes the Synthesis of Compounds of General Formula II.

Scheme 4

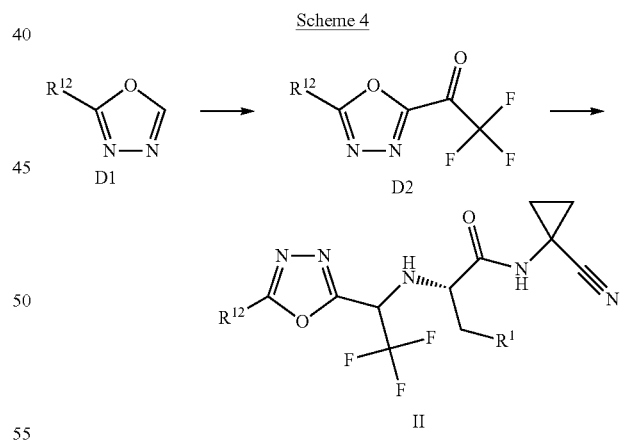

Intermediates of general formula D2 can be obtained starting from commercially available 1,3,4-oxadiazoles of general formula D1 upon treatment with trifluoroacetic anhydride (TFAA) and dimethyl aminopyridine (DMAP). Compounds of general formula II can be obtained via a reductive amination between intermediates D2 and intermediates A4, by treatment with a reducing agent such as TiCl$_4$ or sodium cyanoborohydride in CH$_2$Cl$_2$, preferably sodium cyanoborohydride, affording compounds of general formula II as a mixture of diastereomers. These diastereomers can typically be separated by flash chromatography (FC).

The invention thus also relates to a process for the manufacture of a compound of formula (I) comprising one of the following steps:
(a) the reaction of a compound of formula (A)

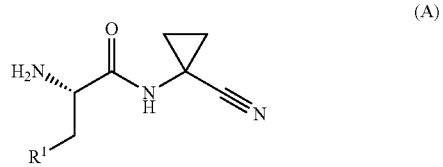

(A)

in the presence of a compound of formula R²COOH, a coupling agent and a base; or
(b) the reaction of a compound of formula (II) as defined above in the presence of R²C(O)CF₃ and a reducing agent.

In step (a), the coupling agent is for example HATU, HBTU or EDCI, in particular HATU.

In step (a), the base is in particular a non-nucleophilic base, more particularly iPr₂Net.

Step (a) can be carried out in a polar aprotic solvent, in particular DMF or DMA, particularly DMF.

Step (a) can be done in particular at 0° C. or 22° C., in particular 0° C.

In step (b), the reducing agent is for example TiCl₄ or sodium cyanoborohydride, in particular sodium cyanoborohydride.

Step (b) can be done in particular in dichloromethane.

The invention thus also relates to a compound of formula (I) when manufactured according to the above process.

The Invention Further Relates to:

A compound of formula (I) for use as a therapeutically active substance;

A pharmaceutical composition comprising a compound of formula (I) and a therapeutically inert carrier;

The use of a compound of formula (I) for the preparation of a medicament for the treatment or prophylaxis of Human African Trypanosomiasis or African Sleeping Sickness;

A compound of formula (I) for use in the treatment or prophylaxis of Human African Trypanosomiasis or African Sleeping Sickness; and A method for the treatment or prophylaxis of Human African Trypanosomiasis or African Sleeping Sickness, which method comprises administering an effective amount of a compound of formula (I) to a patient in need thereof.

Another embodiment of the invention provides a pharmaceutical composition or medicament containing a compound of the invention and a therapeutically inert carrier, diluent or excipient, as well as a method of using the compounds of the invention to prepare such composition and medicament. In one example, the compound of formula (I) may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula (I) is formulated in an acetate buffer, at pH 5. In another embodiment, the compound of formula (I) is sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration. The compounds of the invention may be administered in particular by intravitreal administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

The following examples are provided for illustration of the invention. They should not be considered as limiting the scope of the invention, but merely as being representative thereof.

EXAMPLES

NMR: ¹H NMR spectra were recorded on a Bruker AC-300 or AC-600 spectrometer at 25° C. with TMS (tetramethylsilane) or residual ¹H of the given deuterated solvents as internal standards.

MS: Mass spectra (MS) were measured either with ion spray positive or negative (ISP or ISN) method on a Perkin-Elmer SCIEX API 300 or with electron impact method (EI, 70 eV) on a Finnigan MAT SSQ 7000 spectrometer.

LC-MS (ESI, positive or negative ion) data were recorded on Waters UPLC-MS Systems equipped with Waters Acquity, a CTC PAL auto sampler and a Waters SQD single quadrupole mass spectrometer using ES ionization modes (positive and/or negative). The separation was achieved on a Zorbax Eclipse Plus C18 1.7 µm 2.1×30 mm column at 50°

C.; A=0.01% formic acid in water, B=acetonitrile at flow 1; gradient: 0 min 3% B, 0.2 min 3% B, 2 min 97% B, 1.7 min 97% B, 2.0 min 97% B. The injection volume was 2 μL. MS (ESI, positive or negative ion): FIA (flow injection analysis)-MS were recorded on an AppliedBiosystem API150 mass spectrometer. Sample introduction was made with a CTC PAL auto sampler and a Shimadzu LC-10ADVP Pump. The samples were directly flushed to the ESI source of the mass spectrometer with a flow 50 μL/min of a mixture of acetonitrile and 10 mM ammonium acetate (1:1) without a column. The injection volume was 2 μL.

Abbreviations:
CAN Acetonitrile
Ar Argon
b. *brucei*
Boc Tert-Butoxy carbamate
CAS Chemical Abstracts Services
DEAD Diethyl diazenedicarboxylate
DMA Dimethylacetamide
DMAP 4-Dimethylaminopyridine
DMF Dimethylformamide
EDCI 3-(Ethyliminomethyleneamino)-N,N-dimethylpropan-1-amine
Eq Equivalent(s)
ESI Electrospray Ionization
Et Ethyl
EtOAc Ethyl Acetate
eV Electronvolt(s)
FC Flash Chromatography
Fmoc 9-Fluorenylmethoxycarbonyl
g Gram(s)
h Hour(s)
HATU 1-[Bis(dimethylamino)methylene]-1H-1,2,3-triazolo[4,5-b]pyridinium 3-oxide hexafluorophosphate
HBTU 3-[Bis(dimethylamino)methyliumyl]-3H-benzotriazol-1-oxide hexafluorophosphate
HEPES 2-[4-(2-hydroxyethyl)piperazin-1-yl]ethanesulfonic acid
IC50 Half maximum inhibitory concentration
LC Liquid Chromatography
M Molar
Me Methyl
MEM Minimum Essential Medium
MeOH Methanol
mg Milligram(s)
min Minute(s)
mL Milliliter(s)
mmol Millimole(s)
MPLC Medium Pressure Liquid Chromatography
MS Mass Spectrometry
MW Microwave
N Normal
nm Nanometer(s)
OAc Acetate
PG Protecting Group
RP-HPLC Reverse Phase High Pressure Liquid Chromatography
T. *Trypanosoma*
tBu Tert-Butyl
TLC Thin Layer Chromatography
TFA Trifluoroacetic acid
TFAA Trifluoroacetic anhydride
THF Tetrahydrofuran
TMS Tetramethylsilane
W Watt(s)

Example 1

(S)—N-(3-(3-chloro-4-(trifluoromethoxy)phenyl)-1-(1-cyanocyclopropylamino)-1-oxopropan-2-yl)-1-(2,2-difluoroethyl)-3-(trifluoromethyl)-1H-pyrazole-5-carboxamide a) (2S)-3-[3-chloro-4-(trifluoromethoxy)phenyl]-2-[(2-methylpropan-2-yl)oxycarbonylamino]propanoic Acid

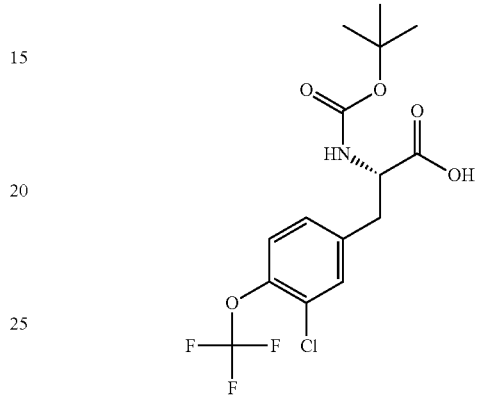

A solution of (S)-2-amino-3-(3-chloro-4-(trifluoromethoxy)phenyl)propanoic acid hydrochloride (3 g, 9.37 mmol, Eq: 1 in 1:1 dioxane was treated with a 1N aqueous sodium hydroxide solution (20.6 ml, 20.6 mmol, Eq: 2.2) and di-tert-butyl dicarbonate (2.25 g, 10.3 mmol, Eq: 1.1) at 22° C. The mixture was stirred for 18 h at this temperature. After this, the mixture was concentrated concentrated in vacuo to remove dioxane. The resulting aqueous solution was acidified to pH 5 with 1N aqueous HCl solution, and EtOAc was added. The phases were separated, and the aqueous phase extracted with EtOAc (3×). The combined organic layers were washed with brine, dried over $Na_2SO_4$, filtered, and evaporated, to give the title compound as a white viscous oil (3.52 g; 98%). MS (ESI): m/z=382.1 [M−H]−.

b) tert-butyl N-[(2S)-3-[3-chloro-4-(trifluoromethoxy)phenyl]-1-[(1-cyanocyclopropyl)amino]-1-oxopropan-2-yl]carbamate

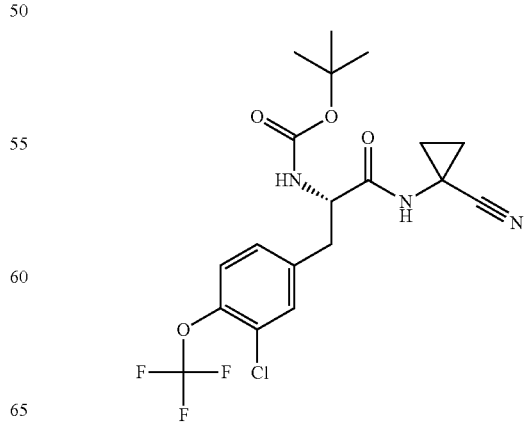

To a solution of (S)-2-((tert-butoxycarbonyl)amino)-3-(3-chloro-4-(trifluoromethoxy)-phenyl)propanoic acid (example 1a; 3.52 g, 9.17 mmol, Eq: 1) in DMF (40 ml) 1-aminocyclopropanecarbonitrile hydrochloride (1.31 g, 11 mmol, Eq: 1.2), HATU (6.98 g, 18.3 mmol, Eq: 2) and iPr$_2$Net (4.15 g, 5.61 ml, 32.1 mmol, Eq: 3.5) were added at 0° C. under an Argon atmosphere. The mixture was stirred for 3 h, during that time to the mixture was warmed up to 25° C. After that the mixture was diluted with EtOAc. The organic phase was extracted with water (2×) and brine (3×), dried over Na$_2$SO$_4$, filtered, and evaporated to dryness. The mixture was purified by flash chromatography (SiO$_2$; CH$_2$Cl$_2$/EtOAc, gradient from 100:0 to 0:100 within 40 min) to yield the title compound (3.14 g; 76.4%) as a yellow solid. MS (ESI): m/z=446.1 [M−H]$^-$.

c) (2S)-2-amino-3-[3-chloro-4-(trifluoromethoxy)phenyl]-N-(1-cyanocyclopropyl)-propanamide

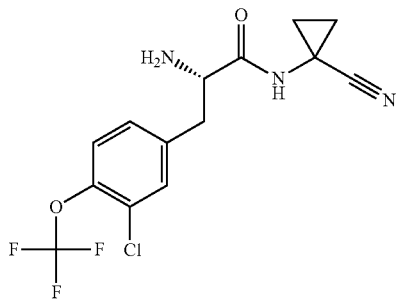 [SMILES: N#CC1(NC(=O)[C@@H](N)Cc2ccc(OC(F)(F)F)c(Cl)c2)CC1]

A solution of (S)-tert-butyl (3-(3-chloro-4-(trifluoromethoxy)phenyl)-1-((1-cyanocyclopropyl)amino)-1-oxopropan-2-yl)carbamate (example 1b; 3.12 g, 6.97 mmol, Eq: 1) in formic acid (18 g, 15 ml, 391 mmol, Eq: 56.1) was stirred at 25° C. for 6 h, before being diluted with 50 mL of water and extracted with CH$_2$Cl$_2$ (1×). The aqueous phase was then basified to pH=9 with NaOH pellets, and the aqueous phase was extracted with CH$_2$Cl$_2$ (3×), dried over Na$_2$SO$_4$, filtered, and evaporated to give the title compound (2.09 g; 86.3%) as a crude yellow oil. MS (ESI): m/z=348.1 [M+H]$^+$.

d) (S)—N-(3-(3-chloro-4-(trifluoromethoxy)phenyl)-1-(1-cyanocyclopropylamino)-1-oxopropan-2-yl)-1-(2,2-difluoroethyl)-3-(trifluoromethyl)-1H-pyrazole-5-carboxamide

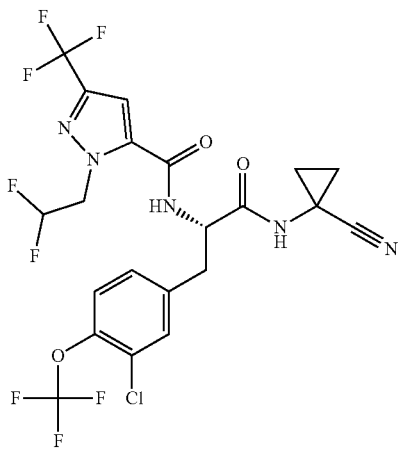 [SMILES: N#CC1(NC(=O)[C@H](Cc2ccc(OC(F)(F)F)c(Cl)c2)NC(=O)c2cc(C(F)(F)F)nn2CC(F)F)CC1]

To a solution of 1-(2,2-difluoroethyl)-3-(trifluoromethyl)-1H-pyrazole-5-carboxylic acid (35 mg, 143 μmol, Eq: 1.00) in DMF (842 μl) was added HATU (109 mg, 287 μmol, Eq: 2), iPr$_2$Net (64.9 mg, 87.6 μl, 502 μmol, Eq: 3.5) and (S)-2-amino-3-(3-chloro-4-(trifluoromethoxy)phenyl)-N-(1-cyanocyclopropyl)propanamide (example 1c; 59.8 mg, 172 μmol, Eq: 1.2), at 22° C., under Ar. The mixture was stirred at this temperature for 1 h, before being quenched with a solution of sat. NaHCO$_3$ (3 mL) and partitioned between 25 mL H$_2$O and 50 mL EtOAc. The phases were separated. The aqueous layer was extracted with EtOAc (2×50 mL). The combined organic layers were washed with sat. NaCl (3×20 mL), dried over MgSO$_4$, filtered and evaporated. FC (SiO$_2$; 40 g, 0% to 50% EtOAc in heptane, 40 ml/min., 254 nm) gave the title compound (50 mg; 60.8%) as light yellow solid. MS (ESI): m/z=572.2 [M−H]$^-$.

Example 2

(S)—N-(3-(3-chloro-4-(trifluoromethoxy)phenyl)-1-(1-cyanocyclopropylamino)-1-oxopropan-2-yl)-1-methyl-3-(trifluoromethyl)-1H-pyrazole-5-carboxamide

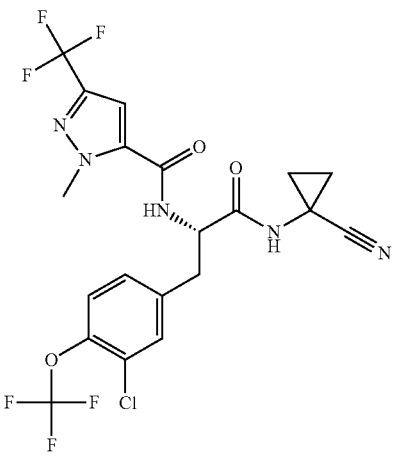 [SMILES: Cn1nc(C(F)(F)F)cc1C(=O)N[C@@H](Cc1ccc(OC(F)(F)F)c(Cl)c1)C(=O)NC1(C#N)CC1]

Example 2 was prepared from 1-methyl-3-(trifluoromethyl)-1H-pyrazole-5-carboxylic acid and (2S)-2-amino-3-[3-chloro-4-(trifluoromethoxy)phenyl]-N-(1-cyanocyclopropyl)-propanamide (example 1c) in analogy to the methods described in examples 1a-d) to yield the title compound as a white solid (60 mg; 80%). MS (ESI): m/z=524.1 [M+H]$^+$.

Example 3

(S)—N-(3-(3-chloro-4-(trifluoromethoxy)phenyl)-1-(1-cyanocyclopropylamino)-1-oxopropan-2-yl)-1,3-dimethyl-1H-pyrazole-5-carboxamide

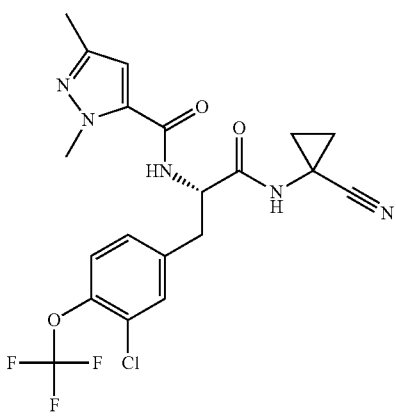 [SMILES: Cc1cc(C(=O)N[C@@H](Cc2ccc(OC(F)(F)F)c(Cl)c2)C(=O)NC2(C#N)CC2)n(C)n1]

Example 3 was prepared from 1,3-dimethyl-1H-pyrazole-5-carboxylic acid and (S)-2-amino-3-(3-chloro-4-(trifluoromethoxy)phenyl)propanoic acid hydrochloride in analogy to the methods described in examples 1a-d) to yield the title compound as a white powder (38 mg; 47%). MS (ESI): m/z=470.1 [M+H]$^+$.

Example 4

(S)—N-(3-(3-chloro-4-(trifluoromethoxy)phenyl)-1-(1-cyanocyclopropylamino)-1-oxopropan-2-yl)-3-cyclopropyl-1-methyl-1H-pyrazole-5-carboxamide

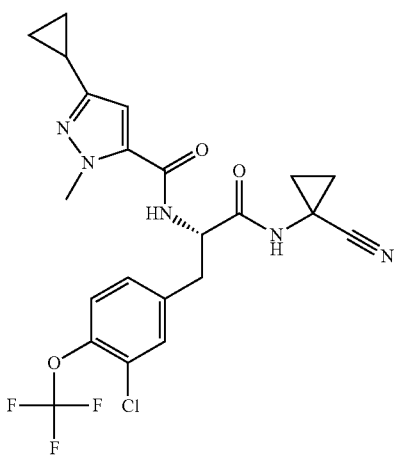 [SMILES: Cn1nc(C2CC2)cc1C(=O)N[C@@H](Cc1ccc(OC(F)(F)F)c(Cl)c1)C(=O)NC1(C#N)CC1]

Example 4 was prepared from 3-cyclopropyl-1-methyl-1H-pyrazole-5-carboxylic acid and (S)-2-amino-3-(3-chloro-4-(trifluoromethoxy)phenyl)propanoic acid hydrochloride in analogy to the methods described in examples 1a-d) to yield the title compound as a white solid (41 mg; 49%). MS (ESI): m/z=496.2 [M+H]$^+$.

Example 5

(S)-3-tert-butyl-N-(3-(3-chloro-4-(trifluoromethoxy)phenyl)-1-(1-cyanocyclopropylamino)-1-oxopropan-2-yl)-1-methyl-1H-pyrazole-5-carboxamide

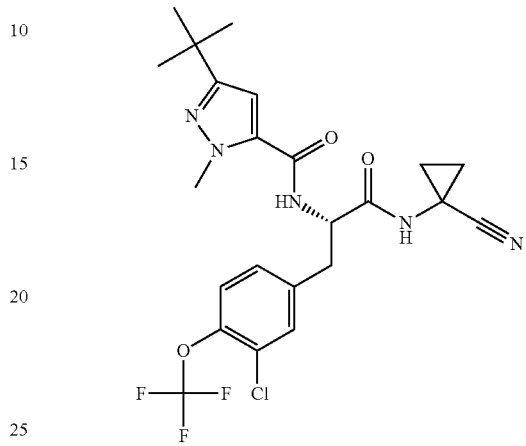

Example 5 was prepared from 3-tert-butyl-1-methyl-1H-pyrazole-5-carboxylic acid and (S)-2-amino-3-(3-chloro-4-(trifluoromethoxy)phenyl)propanoic acid hydrochloride in analogy to the methods described in examples 1a-d) to yield the title compound as a white powder (32 mg; 36%). MS (ESI): m/z=512.2 [M+H]$^+$.

Example 6

(S)—N-(3-(3-chloro-4-(trifluoromethoxy)phenyl)-1-(1-cyanocyclopropylamino)-1-oxopropan-2-yl)-1-(4-fluorophenyl)-1H-pyrazole-3-carboxamide

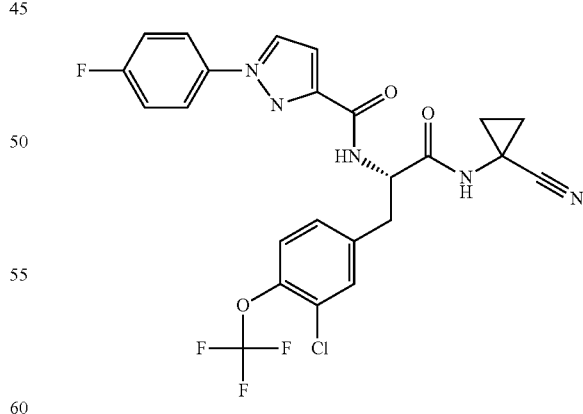

Example 6 was prepared from 1-(4-fluorophenyl)-1H-pyrazole-3-carboxylic acid and (S)-2-amino-3-(3-chloro-4-(trifluoromethoxy)phenyl)propanoic acid hydrochloride in analogy to the methods described in examples 1a-d) to yield the title compound as a white powder (40 mg; 43%). MS (ESI): m/z=536.1 [M+H]$^+$.

Example 7

(S)—N-(3-(3-chloro-4-(trifluoromethoxy)phenyl)-1-(1-cyanocyclopropylamino)-1-oxopropan-2-yl)-1-methyl-3-phenyl-1H-pyrazole-5-carboxamide

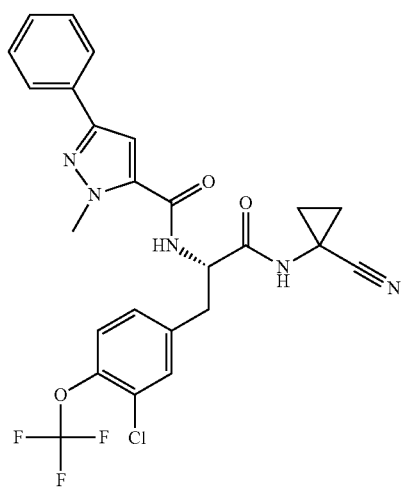 [SMILES: Cn1nc(-c2ccccc2)cc1C(=O)N[C@@H](Cc1ccc(OC(F)(F)F)c(Cl)c1)C(=O)NC1(C#N)CC1]

Example 7 was prepared from 1-methyl-3-phenyl-1H-pyrazole-5-carboxylic acid and (S)-2-amino-3-(3-chloro-4-(trifluoromethoxy)phenyl)propanoic acid hydrochloride in analogy to the methods described in examples 1a-d) to yield the title compound as a white powder (44 mg; 48%). MS (ESI): m/z=532.1 [M+H]$^+$.

Example 8

(S)—N-(3-(3-chloro-4-(trifluoromethoxy)phenyl)-1-(1-cyanocyclopropylamino)-1-oxopropan-2-yl)-2-(4-chlorophenyl)-5-methyloxazole-4-carboxamide

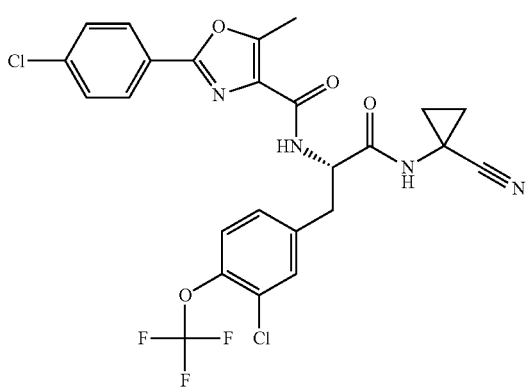 [SMILES: Cc1oc(-c2ccc(Cl)cc2)nc1C(=O)N[C@@H](Cc1ccc(OC(F)(F)F)c(Cl)c1)C(=O)NC1(C#N)CC1]

Example 8 was prepared from 2-(4-chlorophenyl)-5-methyloxazole-4-carboxylic acid and (S)-2-amino-3-(3-chloro-4-(trifluoromethoxy)phenyl)propanoic acid hydrochloride in analogy to the methods described in examples 1a-d) to yield the title compound as an off-white solid (47 mg; 48%). MS (ESI): m/z=567.1 [M+H]$^+$.

Example 9

(S)—N-(3-(3-chloro-4-(trifluoromethoxy)phenyl)-1-(1-cyanocyclopropylamino)-1-oxopropan-2-yl)-2-(4-fluorophenyl)-2H-1,2,3-triazole-4-carboxamide

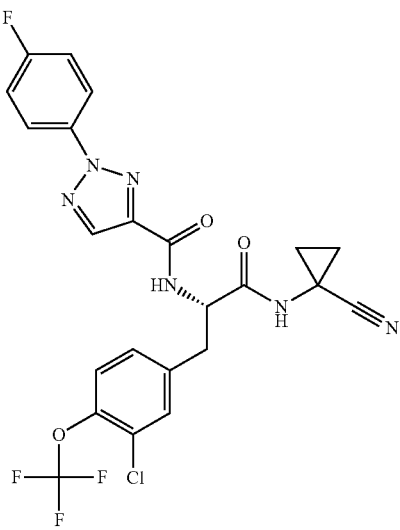 [SMILES: N#CC1(NC(=O)[C@H](Cc2ccc(OC(F)(F)F)c(Cl)c2)NC(=O)c2cnn(-c3ccc(F)cc3)n2)CC1]

Example 9 was prepared from 2-(4-fluorophenyl)-2H-1,2,3-triazole-4-carboxylic acid and (S)-2-amino-3-(3-chloro-4-(trifluoromethoxy)phenyl)propanoic acid hydrochloride in analogy to the methods described in examples 1a-d) to yield the title compound as a white powder (42 mg; 46%). MS (ESI): m/z=537.2 [M+H]$^+$.

Example 10

(S)—N-(3-(3-chloro-4-(trifluoromethoxy)phenyl)-1-(1-cyanocyclopropylamino)-1-oxopropan-2-yl)-3-(2-chlorophenyl)-1H-pyrazole-5-carboxamide

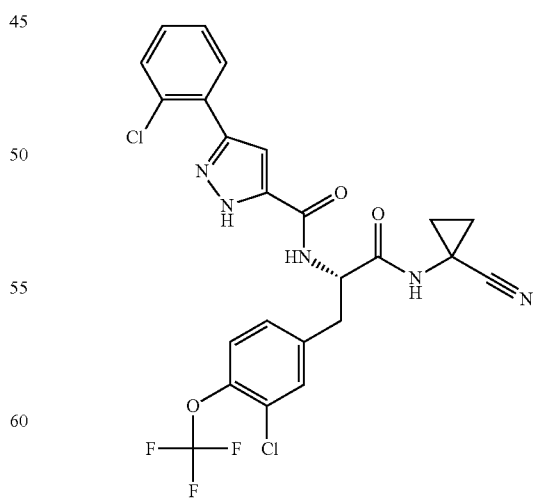

Example 10 was prepared from 3-(2-chlorophenyl)-1H-pyrazole-5-carboxylic acid and (S)-2-amino-3-(3-chloro-4-(trifluoromethoxy)phenyl)propanoic acid hydrochloride in

Example 11

(S)—N-(3-(3-chloro-4-(trifluoromethoxy)phenyl)-1-(1-cyanocyclopropylamino)-1-oxopropan-2-yl)-3-(4-fluorophenyl)-1H-pyrazole-5-carboxamide

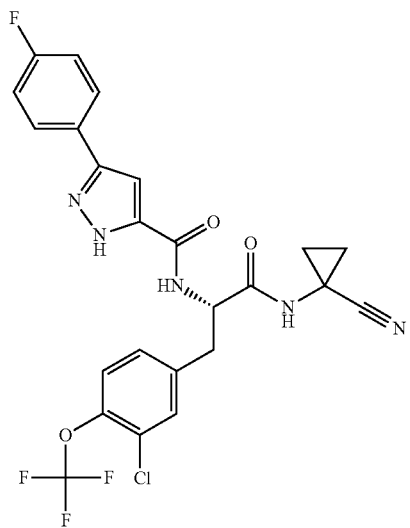 [SMILES: N#CC1(NC(=O)[C@H](Cc2ccc(OC(F)(F)F)c(Cl)c2)NC(=O)c2cc(-c3ccc(F)cc3)n[nH]2)CC1]

Example 11 was prepared from 3-(4-fluorophenyl)-1H-pyrazole-5-carboxylic acid and (S)-2-amino-3-(3-chloro-4-(trifluoromethoxy)phenyl)propanoic acid hydrochloride in analogy to the methods described in examples 1a-d) to yield the title compound as a white solid (19 mg; 21%). MS (ESI): m/z=536.2 [M+H]$^+$.

Example 12

(S)—N-(3-(3-chloro-4-(trifluoromethoxy)phenyl)-1-(1-cyanocyclopropylamino)-1-oxopropan-2-yl)-3-(4-methoxyphenyl)-1H-pyrazole-5-carboxamide

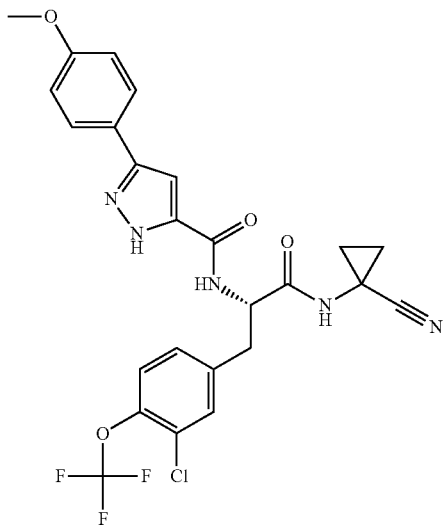 [SMILES: COc1ccc(-c2cc(C(=O)N[C@@H](Cc3ccc(OC(F)(F)F)c(Cl)c3)C(=O)NC3(C#N)CC3)[nH]n2)cc1]

Example 12 was prepared from 3-(4-methoxyphenyl)-1H-pyrazole-5-carboxylic acid and (S)-2-amino-3-(3-chloro-4-(trifluoromethoxy)phenyl)propanoic acid hydrochloride in analogy to the methods described in examples 1a-d) to yield the title compound as a white solid (6 mg; 6%). MS (ESI): m/z=548.2 [M+H]$^+$.

Example 13

(S)—N-(3-(3-chloro-4-(trifluoromethoxy)phenyl)-1-(1-cyanocyclopropylamino)-1-oxopropan-2-yl)-3-phenylisoxazole-5-carboxamide

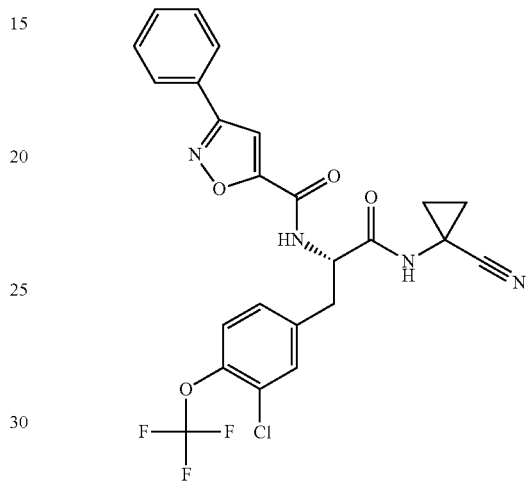

Example 13 was prepared from 3-phenylisoxazole-5-carboxylic acid and (S)-2-amino-3-(3-chloro-4-(trifluoromethoxy)phenyl)propanoic acid hydrochloride in analogy to the methods described in examples 1a-d) to yield the title compound as an off-white solid (27 mg; 30%). MS (ESI): m/z=519.1 [M+H]$^+$.

Example 14

(S)—N-(3-(3-chloro-4-(trifluoromethoxy)phenyl)-1-(1-cyanocyclopropylamino)-1-oxopropan-2-yl)-5-methyl-2-phenyl-2H-1,2,3-triazole-4-carboxamide

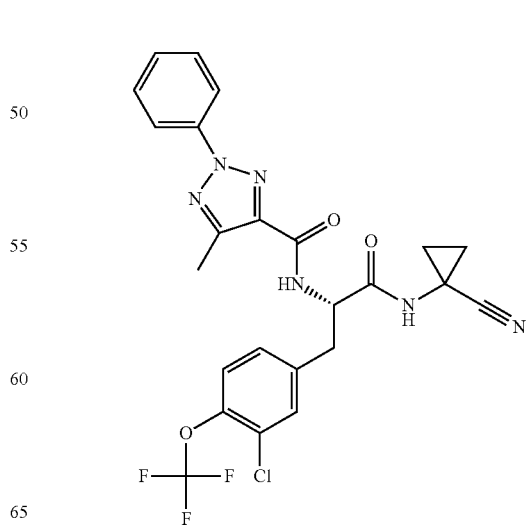

Example 14 was prepared from 5-methyl-2-phenyl-2H-1,2,3-triazole-4-carboxylic acid and (S)-2-amino-3-(3-chloro-4-(trifluoromethoxy)phenyl)propanoic acid hydrochloride in analogy to the methods described in examples 1a-d) to yield the title compound as a white solid (31 mg; 34%). MS (ESI): m/z=533.1 [M+H]$^+$.

Example 15

(S)—N-(3-(3-chloro-4-(trifluoromethoxy)phenyl)-1-(1-cyanocyclopropylamino)-1-oxopropan-2-yl)-5-(3-fluorophenyl)-1,2,4-oxadiazole-3-carboxamide

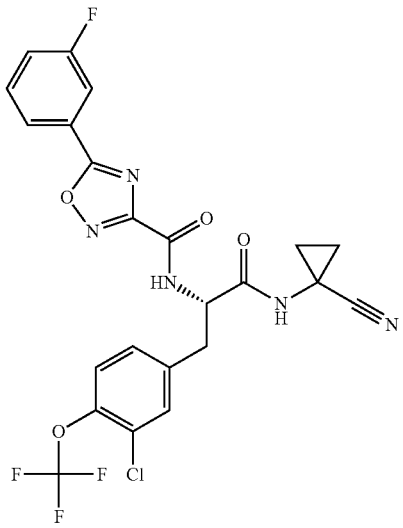 [SMILES: N#CC1(NC(=O)[C@H](Cc2ccc(OC(F)(F)F)c(Cl)c2)NC(=O)c2noc(-c3cccc(F)c3)n2)CC1]

Example 15 was prepared from 5-(3-fluorophenyl)-1,2,4-oxadiazole-3-carboxylic acid and (S)-2-amino-3-(3-chloro-4-(trifluoromethoxy)phenyl)propanoic acid hydrochloride in analogy to the methods described in examples 1a-d) to yield the title compound as a white solid (11 mg; 12%). MS (ESI): m/z=536.2 [M−H]$^-$.

Example 16

(S)—N-(3-(3-chloro-4-(trifluoromethoxy)phenyl)-1-(1-cyanocyclopropylamino)-1-oxopropan-2-yl)-2-phenyl-2H-1,2,3-triazole-4-carboxamide

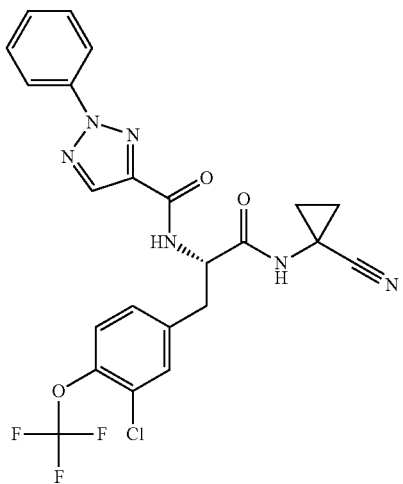 [SMILES: N#CC1(NC(=O)[C@H](Cc2ccc(OC(F)(F)F)c(Cl)c2)NC(=O)c2cnn(-c3ccccc3)n2)CC1]

Example 16 was prepared from 2-phenyl-2H-1,2,3-triazole-4-carboxylic acid and (S)-2-amino-3-(3-chloro-4-(trifluoromethoxy)phenyl)propanoic acid hydrochloride in analogy to the methods described in examples 1a-d) to yield the title compound as a white solid (38 mg; 42%). MS (ESI): m/z=519.2 [M+H]$^+$.

Example 17

(S)—N-(3-(3-chloro-4-(trifluoromethoxy)phenyl)-1-(1-cyanocyclopropylamino)-1-oxopropan-2-yl)-3-(3-chlorophenyl)-1-methyl-1H-pyrazole-5-carboxamide

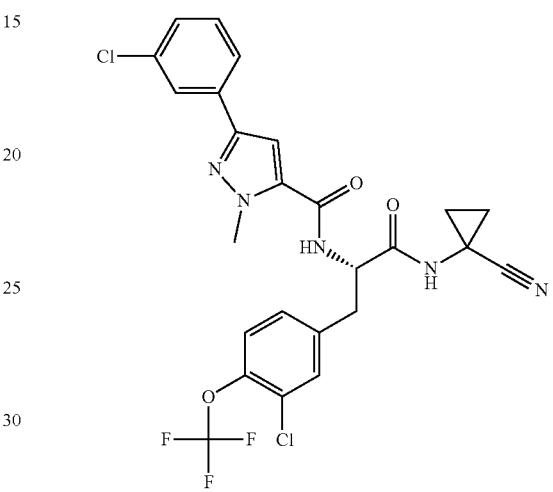

Example 17 was prepared from 3-(3-chlorophenyl)-1-methyl-1H-pyrazole-5-carboxylic acid and (S)-2-amino-3-(3-chloro-4-(trifluoromethoxy)phenyl)propanoic acid hydrochloride in analogy to the methods described in examples 1a-d) to yield the title compound as a light yellow solid (71 mg; 87%). MS (ESI): m/z=566.2 [M+H]$^+$.

Example 18

(S)—N-(3-(3-chloro-4-(trifluoromethoxy)phenyl)-1-(1-cyanocyclopropylamino)-1-oxopropan-2-yl)-5-(3-chlorophenyl)-1,2,4-oxadiazole-3-carboxamide

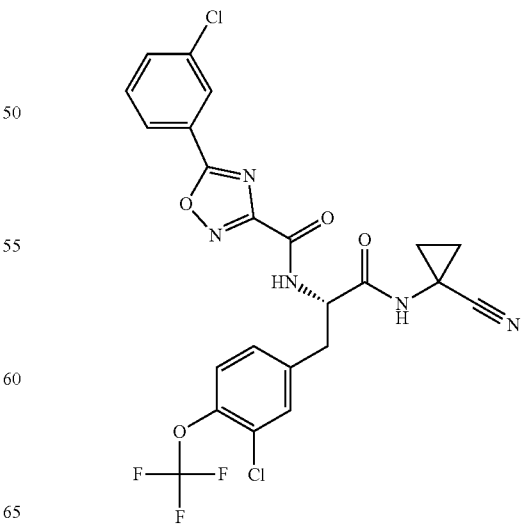

Example 18 was prepared from 5-(3-chlorophenyl)-1,2,4-oxadiazole-3-carboxylic acid and (S)-2-amino-3-(3-chloro-4-(trifluoromethoxy)phenyl)propanoic acid hydrochloride in analogy to the methods described in examples 1a-d) to yield the title compound as a white solid (52 mg; 73%). MS (ESI): m/z=552.2 [M–H]⁻.

Example 19

(2S)-2-[[1-[5-(4-bromophenyl)-1,3,4-oxadiazol-2-yl]-2,2,2-trifluoroethyl]amino]-3-[3-chloro-4-(trifluoromethoxy)phenyl]-N-(1-cyanocyclopropyl)propanamide; 1 Epimer, Entity B a) 1-(5-(4-bromophenyl)-1,3,4-oxadiazol-2-yl)-2,2,2-trifluoroethanone

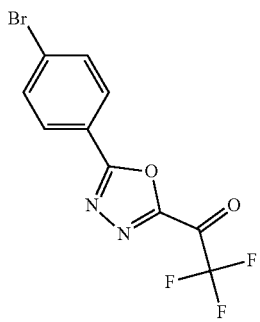 [SMILES: O=C(c1nnc(-c2ccc(Br)cc2)o1)C(F)(F)F]

A solution of 2-(4-bromophenyl)-1,3,4-oxadiazole (100 mg, 444 mol, Eq: 1.00) in CH$_2$Cl$_2$ (5.00 ml) was treated with trifluoroacetic anhydride (233 mg, 157 µl, 1.11 mmol, Eq: 2.5) and DMAP (27.1 mg, 222 mol, Eq: 0.5) at 22° C., under Ar. The mixture was stirred at this temperature for 40 h. The reaction progress was monitored by TLC (SiO$_2$; hexane/EtOAC 1:1) showing the reaction was incomplete with starting material remaining. The reaction mixture was evaporated and the crude residue was purified by FC (silica gel, 12 g, heptane/EtOAc, gradient from 100:0 ti 80:20 within 30 min) to give the title compound (35 mg; 25%) as yellow solid. MS (ESI): m/z=321.0 [M–H]⁻.

b) (2S)-2-[[1-[5-(4-bromophenyl)-1,3,4-oxadiazol-2-yl]-2,2,2-trifluoroethyl]amino]-3-[3-chloro-4-(trifluoromethoxy)phenyl]-N-(1-cyanocyclopropyl)propanamide; 1 Epimer, Entity B

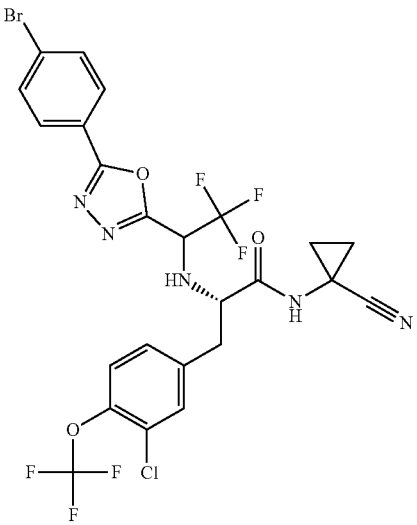 [SMILES: N#CC1(NC(=O)[C@H](Cc2ccc(OC(F)(F)F)c(Cl)c2)NC(c2nnc(-c3ccc(Br)cc3)o2)C(F)(F)F)CC1]

(S)-2-amino-3-(3-chloro-4-(trifluoromethoxy)phenyl)-N-(1-cyanocyclopropyl)propanamide (example 1c) (20 mg, 57.5 mol, Eq: 1.00), 1-(5-(4-bromophenyl)-1,3,4-oxadiazol-2-yl)-2,2,2-trifluoroethanone (18.5 mg, 57.5 mol, Eq: 1.00) and iPr$_2$Net (26.0 mg, 35.2 µl, 201 mol, Eq: 3.50) were dissolved in CH$_2$Cl$_2$ (536 µl). Titanium tetrachloride (18.5 mg, 10.8 µl, 97.8 mol, Eq: 1.7) was added dropwise under nitrogen over 2 min. After 15 min a LC/MS analysis showed the reaction was incomplete with starting material remaining. A solution of sodium cyanoborohydride (11.6 mg, 184 mol, Eq: 3.20) in MeOH (536 µl) was added which made the mixture foam and formed a gas. The mixture was stirred for another 30 min., before being partitioned between 50 mL EtOAc and 50 mL H$_2$O. The phases were separated. The aqueous layer was extracted with EtOAc (2×25 mL). The combined organic layers were washed with sat NaCl (1×25 mL), dried over MgSO$_4$, filtered, and evaporated. The crude material was purified by FC (silica gel, 12 g, 0% to 40% EtOAc in heptane, 30 ml/min., 254 nm) to give the title compound (3.8 mg; 10%) as yellow solid. MS (ESI): m/z=654.1 [M+H]⁺.

Example 20

(2S)-2-(1-(5-(4-bromophenyl)-1,3,4-oxadiazol-2-yl)-2,2,2-trifluoroethylamino)-3-(3-chloro-4-(trifluoromethoxy)phenyl)-N-(1-cyanocyclopropyl)propanamide; 1 Epimer, Entity A

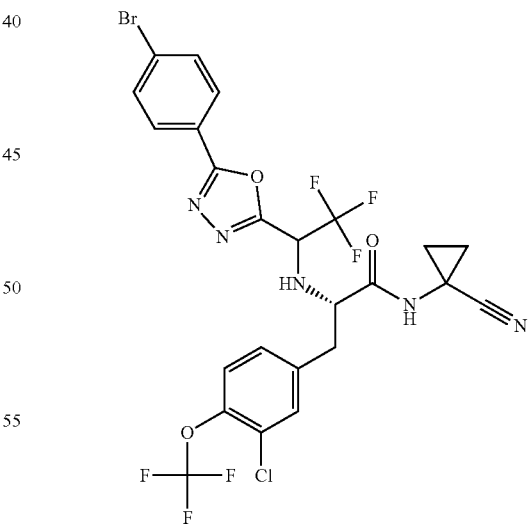

Example 20 was prepared from 1-(5-(4-bromophenyl)-1,3,4-oxadiazol-2-yl)-2,2,2-trifluoroethanone (example 19a) and (2S)-2-amino-3-[3-chloro-4-(trifluoromethoxy)phenyl]-N-(1-cyanocyclopropyl)-propanamide (example 1c) in analogy to the methods described in example 19b to yield the title compound as a yellow solid (6 mg; 16%). MS (ESI): m/z=654.1 [M+H]⁺.

Example 21

(2S)-3-(3-chloro-4-(trifluoromethoxy)phenyl)-N-(1-cyanocyclopropyl)-2-(2,2,2-trifluoro-1-(5-phenyl-1,3,4-oxadiazol-2-yl)ethylamino)propanamide; 1 epimer, entity A

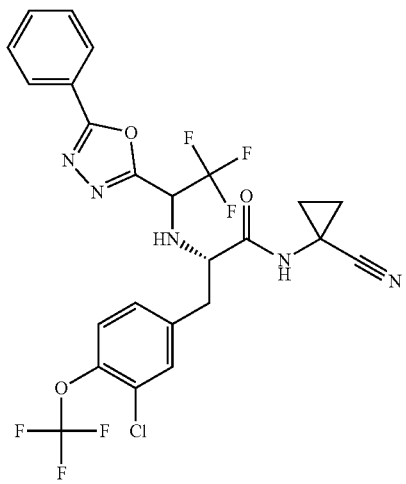 [SMILES: N#CC1(NC(=O)[C@H](Cc2ccc(OC(F)(F)F)c(Cl)c2)NC(c2nnc(-c3ccccc3)o2)C(F)(F)F)CC1]

Example 21 was prepared from 2-phenyl-1,3,4-oxadiazole and (2S)-2-amino-3-[3-chloro-4-(trifluoromethoxy)phenyl]-N-(1-cyanocyclopropyl)-propanamide (example 1c) in analogy to the methods described in examples 19a-b to yield the title compound as a light yellow amorphous solid (4 mg; 8%). MS (ESI): m/z=574.1 [M+H]$^+$.

Example 22

(2S)-3-(3-chloro-4-(trifluoromethoxy)phenyl)-N-(1-cyanocyclopropyl)-2-(2,2,2-trifluoro-1-(5-phenyl-1,3,4-oxadiazol-2-yl)ethylamino)propanamide; 1 Epimer, Entity B

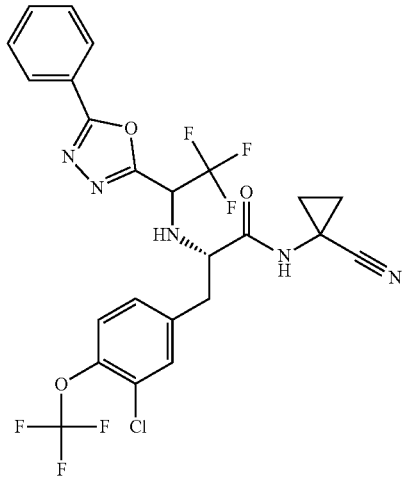 [SMILES: N#CC1(NC(=O)[C@H](Cc2ccc(OC(F)(F)F)c(Cl)c2)NC(c2nnc(-c3ccccc3)o2)C(F)(F)F)CC1]

Example 22 was prepared from 2-phenyl-1,3,4-oxadiazole and (2S)-2-amino-3-[3-chloro-4-(trifluoromethoxy)phenyl]-N-(1-cyanocyclopropyl)-propanamide (example 1c) in analogy to the methods described in examples 19a-b to yield the title compound as a light yellow amorphous solid (7 mg; 14%). MS (ESI): m/z=574.1 [M+H]$^+$.

Example 23

N-[(2S)-3-[3-chloro-4-(trifluoromethoxy)phenyl]-1-[(1-cyanocyclopropyl)amino]-1-oxopropan-2-yl]-2-(4-methylsulfanylphenyl)triazole-4-carboxamide a) ethyl 1H-1,2,3-triazole-4-carboxylate

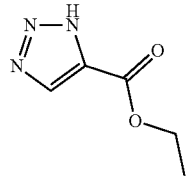

On a Vapourtec R2+/R4 flow system equipped with three PTFA reactor coils (a 10 mL) and a 250 psi back pressure regulator, ethyl propiolate and trimethylsilyl azide were injected via 2 mL loops. The flow rate was set to 0.5 mL/min, with a residence time of 1.5 h. The system was heated to 140° C. Injections were performed every 40 min. The solvent used was acetonitrile. The total mixture coming out of the reactor was collected. In total, 5 injections were performed. The mixture was collected, and acetonitrile removed in vacuo (the collector of the rotary evaporator was filled with sat. aq. NaHCO$_3$ to quench any potentially formed HN$_3$). The remaining solid was dissolved in EtOAc, and the organic phase washed with brine (3×), dried over Na$_2$SO$_4$, filtered, and evaporated. The crude product was stirred in a minimal amount of Et$_2$O, filtered, and dried, to give the title compound (8.65 g, 81%) as a white solid. MS (ESI): m/z=142.1 [M+H]$^+$.

b) ethyl 2-(4-methylsulfanylphenyl)triazole-4-carboxylate

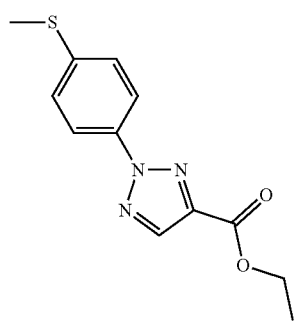 [SMILES: CCOC(=O)c1cnn(-c2ccc(SC)cc2)n1]

A dried flask was equipped with a magnetic stir bar and charged with [Pd$_2$(dba)$_3$] (22.5 mg, 24.6 µmol, Eq: 0.01) and di-tert-butyl(2',4',6'-triisopropyl-3,4,5,6-tetramethyl-[1,1'-biphenyl]-2-yl)phosphine (23.7 mg, 49.2 µmol, Eq: 0.02). The flask was evacuated and backfilled with Ar (3×). Toluene (1.5 mL) was added, and the resulting mixture was stirred for 3 min at 120° C. (until the colour turns from dark-purple to dark brown). A second previously dried flask was equipped with a stir bar, and charged with K$_3$PO$_4$ (1.05 g, 4.92 mmol, Eq: 2) and ethyl 2H-1,2,3-triazole-4-carboxylate (example 23a; 417 mg, 2.95 mmol, Eq: 1.2). The flask was evacuated and filled with Ar. (4-Bromophenyl)(methyl)sulfane (500 mg, 2.46 mmol, Eq: 1) was then added, as well as the premixed catalyst solution and toluene (1.5 mL). The resulting mixture was heated at 120° C. for 4.5 h. The reaction was cooled down to 25° C., diluted with EtOAc, washed with brine, dried over Na$_2$SO$_4$, filtered, and evaporated. MPLC (SiO$_2$; heptane/EtOAc, gradient from 100:0 to 50:50 within 20 min) gave the title compound (196 mg, 30%) as a yellow solid. MS (ESI): m/z=264.1 [M+H]$^+$.

c) 2-(4-(methylthio)phenyl)-2H-1,2,3-triazole-4-carboxylic Acid

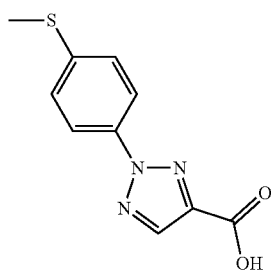 [SMILES: CSc1ccc(-n2ncc(C(=O)O)n2)cc1]

A solution of ethyl 2-(4-methylsulfanylphenyl)triazole-4-carboxylate (example 23b; 196 mg, 744 µmol, Eq: 1) in 2:2:1 THF (2.5 ml)/MeOH (2.5 ml)/H$_2$O (1.25 ml) was treated with LiOH (35.7 mg, 1.49 mmol, Eq: 2), at 25° C. The resulting mixture was stirred for 2 h, before being poured onto 0.1N aq. HCl solution (10 mL). The resulting aqueous layer was washed with EtOAc (3×), and the combined organic layers were dried over Na$_2$SO$_4$, filtered, and evaporated, to give the title compound (164 mg, 94%) as an off-white solid. MS (ESI): m/z=234.1 [M−H]$^−$.

d) N-[(2S)-3-[3-chloro-4-(trifluoromethoxy)phenyl]-1-[(1-cyanocyclopropyl)amino]-1-oxopropan-2-yl]-2-(4-methylsulfanylphenyl)triazole-4-carboxamide

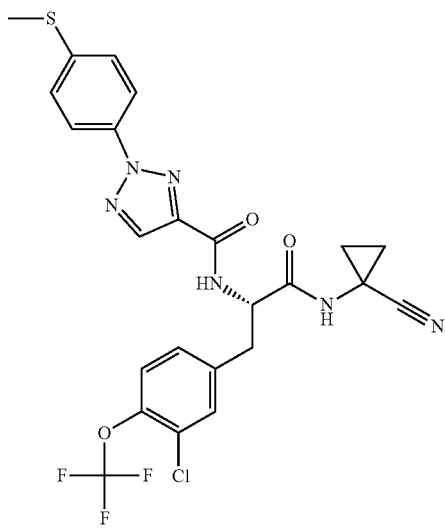 [SMILES: CSc1ccc(-n2ncc(C(=O)N[C@@H](Cc3ccc(OC(F)(F)F)c(Cl)c3)C(=O)NC3(C#N)CC3)n2)cc1]

Example 23d was prepared from 2-(4-(methylthio)phenyl)-2H-1,2,3-triazole-4-carboxylic acid (example 23c) and (2S)-2-amino-3-[3-chloro-4-(trifluoromethoxy)phenyl]-N-(1-cyanocyclopropyl)-propanamide (example 1c) in analogy to the methods described in examples 1a-d) to yield the title compound as an off-white solid (250 mg; 64%). MS (ESI): m/z=563.3 [M−H]$^−$.

Example 24

2-(4-chlorophenyl)-N-[(2S)-3-[3-chloro-4-(trifluoromethoxy)phenyl]-1-[(1-cyanocyclopropyl)amino]-1-oxopropan-2-yl]triazole-4-carboxamide

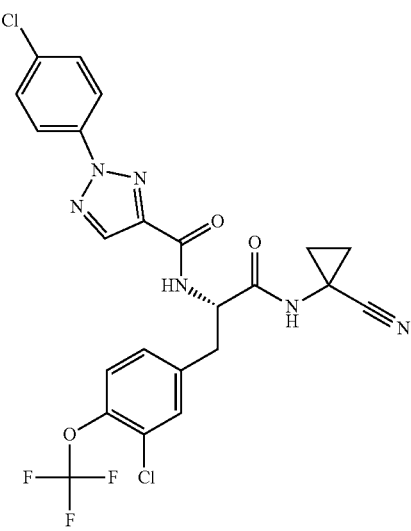 [SMILES: N#CC1(NC(=O)[C@H](Cc2ccc(OC(F)(F)F)c(Cl)c2)NC(=O)c2cnn(-c3ccc(Cl)cc3)n2)CC1]

Example 24 was prepared from 4-chlorobromobenzene and (S)-2-amino-3-(3-chloro-4-(trifluoromethoxy)phenyl)propanoic acid hydrochloride in analogy to the methods described in examples 23b-d) to yield the title compound as a white solid (220 mg; 60%). MS (ESI): m/z=554.1 [M+H]$^+$.

Example 25

N-[(2S)-3-(3-chlorophenyl)-1-[(1-cyanocyclopropyl)amino]-1-oxopropan-2-yl]-2-(4-fluorophenyl)triazole-4-carboxamide

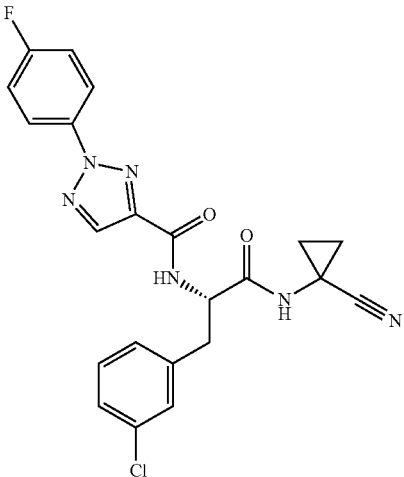 [SMILES: N#CC1(NC(=O)[C@H](Cc2cccc(Cl)c2)NC(=O)c2cnn(-c3ccc(F)cc3)n2)CC1]

Example 25 was prepared from 2-(4-fluorophenyl)-2H-1,2,3-triazole-4-carboxylic acid and (S)-2-amino-3-(3-chlorophenyl)propanoic acid (CAS: 80126-51-8) in analogy to the methods described in examples 1a-d) to yield the title compound as a white solid (76 mg; 25%). MS (ESI): m/z=451.4 [M−H]⁻.

Example 26

N-[(2S)-3-[3-chloro-4-(trifluoromethoxy)phenyl]-1-[(1-cyanocyclopropyl)amino]-1-oxopropan-2-yl]-2-pyridin-3-yltriazole-4-carboxamide

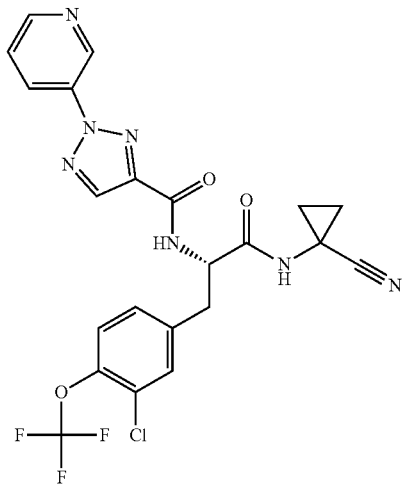 [SMILES: N#CC1(NC(=O)[C@H](Cc2ccc(OC(F)(F)F)c(Cl)c2)NC(=O)c2cnn(-c3cccnc3)n2)CC1]

Example 26 was prepared from 3-bromopyridine and (S)-2-amino-3-(3-chloro-4-(trifluoromethoxy)phenyl)propanoic acid hydrochloride in analogy to the methods described in examples 23b-d to yield the title compound as a white solid (48 mg; 35%). MS (ESI): m/z=520.2 [M+H]⁺.

Example 27

N-[(2S)-1-[(1-cyanocyclopropyl)amino]-1-oxo-3-phenylpropan-2-yl]-2-(4-fluorophenyl)triazole-4-carboxamide

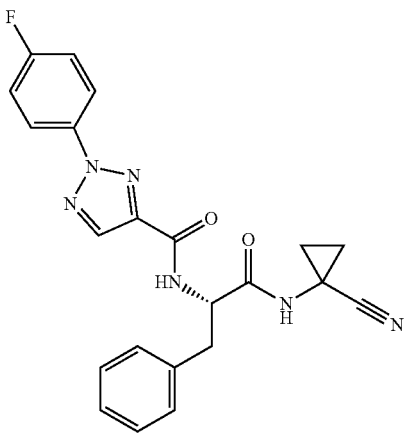

Example 27 was prepared from 2-(4-fluorophenyl)-2H-1,2,3-triazole-4-carboxylic acid and (S)-2-((tert-butoxycarbonyl)amino)-3-phenylpropanoic acid (CAS: 13734-34-4) in analogy to the methods described in examples 1b-d) to yield the title compound as a white solid (173 mg; 77%). MS (ESI): m/z=419.3 [M+H]⁺.

Example 28

N-[(2S)-3-[3-chloro-4-(cyclopropylmethoxy)phenyl]-1-[(1-cyanocyclopropyl)amino]-1-oxopropan-2-yl]-2-(4-fluorophenyl)triazole-4-carboxamide a) cyclopropylmethyl (2S)-3-[3-chloro-4-(cyclopropylmethoxy)phenyl]-2-[(2-methylpropan-2-yl)oxycarbonylamino]propanoate

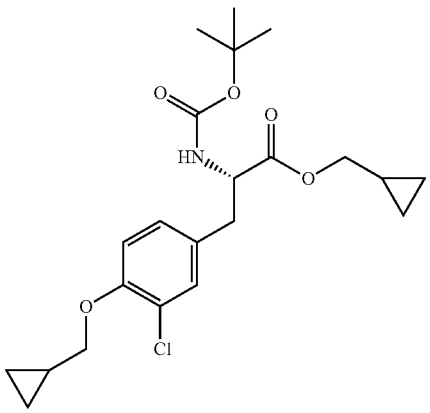 [SMILES: CC(C)(C)OC(=O)N[C@@H](Cc1ccc(OCC2CC2)c(Cl)c1)C(=O)OCC1CC1]

A solution of dicyclohexylamine (S)-2-((tert-butoxycarbonyl)amino)-3-(3-chloro-4-hydroxyphenyl)propanoate (300 mg, 604 mol, Eq: 1) in DMF (5 ml) was treated with Cs₂CO₃ (688 mg, 2.11 mmol, Eq: 3.5) at 25° C., under Ar. The resulting mixture was stirred for 5 min at this temperature, before being treated with (bromomethyl)cyclopropane (285 mg, 207 µl, 2.11 mmol, Eq: 3.5). The mixture was stirred for another 18.5 h, before being diluted with EtOAc. The organic layer was washed with brine (3×), dried over Na₂SO₄, filtered, and evaporated. MPLC (SiO₂; heptane/EtOAc, gradient from 100: to 50:50 within 30 min) gave (S)-cyclopropylmethyl 2-((tert-butoxycarbonyl)amino)-3-(3-chloro-4-(cyclopropylmethoxy)phenyl)propanoate (212 mg, 400 µmol, 66.3% yield) as a colorless oil. MS (ESI): m/z=324.2 [M+H-Boc]⁺.

b) (2S)-2-(tert-butoxycarbonylamino)-3-[3-chloro-4-(cyclopropylmethoxy)phenyl]propanoic Acid

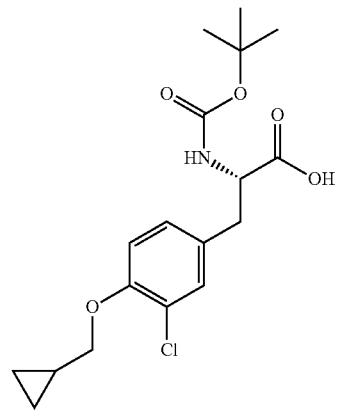 [SMILES: CC(C)(C)OC(=O)N[C@@H](Cc1ccc(OCC2CC2)c(Cl)c1)C(=O)O]

Example 28b was prepared in analogy to the method described in example 23c to give the title compound (140 mg, 100%) as a colorless oil. MS (ESI): m/z=368.3 [M−H]⁻.

c) N-[(2S)-3-[3-chloro-4-(cyclopropylmethoxy)phenyl]-1-[(1-cyanocyclopropyl)amino]-1-oxopropan-2-yl]-2-(4-fluorophenyl)triazole-4-carboxamide

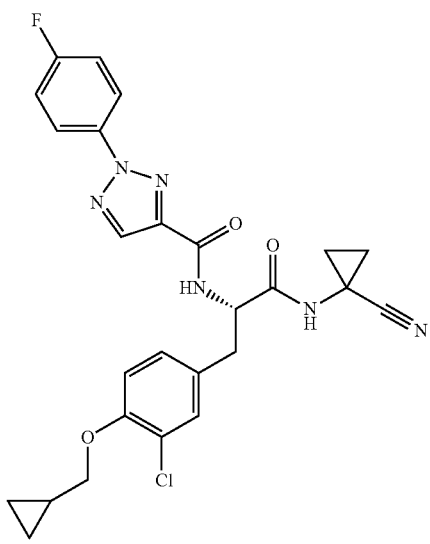 [SMILES: N#CC1(NC(=O)[C@H](Cc2ccc(OCC3CC3)c(Cl)c2)NC(=O)c2cnn(-c3ccc(F)cc3)n2)CC1]

Example 28c was prepared from 2-(4-fluorophenyl)-2H-1,2,3-triazole-4-carboxylic acid and (2S)-2-(tert-butoxycarbonylamino)-3-[3-chloro-4-(cyclopropylmethoxy)phenyl]propanoic acid (example 28b) in analogy to the methods described in examples 1b-d) to yield the title compound as a white solid (31 mg; 24%). MS (ESI): m/z=523.4 [M+H]⁺.

Example 29

N-[(2S)-1-[(1-cyanocyclopropyl)amino]-3-(3,4-dichlorophenyl)-1-oxopropan-2-yl]-2-(4-fluorophenyl)triazole-4-carboxamide

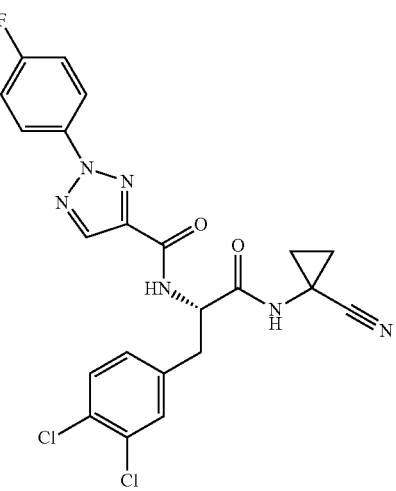

Example 29 was prepared from 2-(4-fluorophenyl)-2H-1,2,3-triazole-4-carboxylic acid and (S)-2-amino-3-(3,4-dichlorophenyl)propanoic acid) (CAS: 52794-99-7) in analogy to the methods described in examples 1a-d) to yield the title compound as a white solid (63 mg; 34%). MS (ESI): m/z=487.2 [M+H]⁺.

Example 30

N-[(2S)-3-[3-chloro-4-(trifluoromethoxy)phenyl]-1-[(1-cyanocyclopropyl)amino]-1-oxopropan-2-yl]-2-(6-fluoropyridin-3-yl)triazole-4-carboxamide a) ethyl 2-(6-fluoropyridin-3-yl)-2H-1,2,3-triazole-4-carboxylate

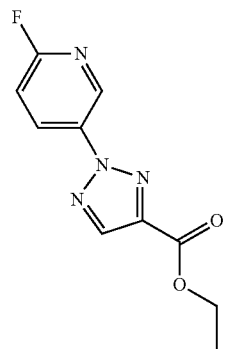 [SMILES: CCOC(=O)c1cnn(-c2ccc(F)nc2)n1]

A solution of ethyl 1H-1,2,3-triazole-5-carboxylate (Example 23a; 500 mg, 3.54 mmol, Eq: 1) and (6-fluoropyridin-3-yl)boronic acid (998 mg, 7.09 mmol, Eq: 2) in DMF (30 mL) was treated with copper (II) acetate (1.29 g, 7.09 mmol, Eq: 2) and pyridine (560 mg, 573 µL, 7.09 mmol, Eq: 2), at 25° C., under air. The mixture was stirred for 72 h at this temperature, before being filtered through a silica plug. The filtrated was evaporated. MPLC (SiO$_2$; heptane/EtOAc, gradient from 100:0 to 50:50 within 30 min) gave the title compound (30 mg, 4%) as a white solid. MS (ESI): m/z=237.1 [M+H]$^+$.

b) N-[(2S)-3-[3-chloro-4-(trifluoromethoxy)phenyl]-1-[(1-cyanocyclopropyl)amino]-1-oxopropan-2-yl]-2-(6-fluoropyridin-3-yl)triazole-4-carboxamide

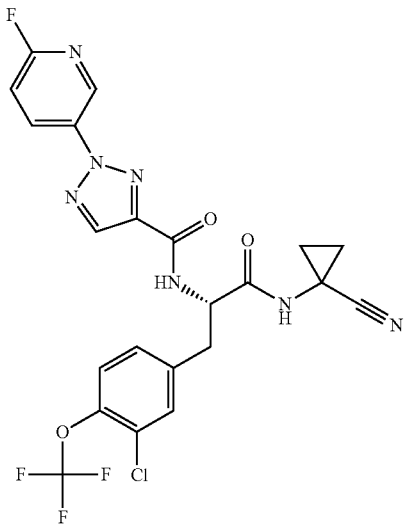

Example 30b was prepared from ethyl 2-(6-fluoropyridin-3-yl)-2H-1,2,3-triazole-4-carboxylate (example 30a) and (S)-2-amino-3-(3-chloro-4-(trifluoromethoxy)phenyl)propanoic acid hydrochloride in analogy to the methods described in examples 23c-d to yield the title compound as a white solid (22 mg; 28%). MS (ESI): m/z=538.2 [M+H]$^+$.

Example 31

N-[(2S)-1-[(1-cyanocyclopropyl)amino]-1-oxo-3-(4-phenylmethoxyphenyl)propan-2-yl]-2-(4-fluorophenyl)triazole-4-carboxamide

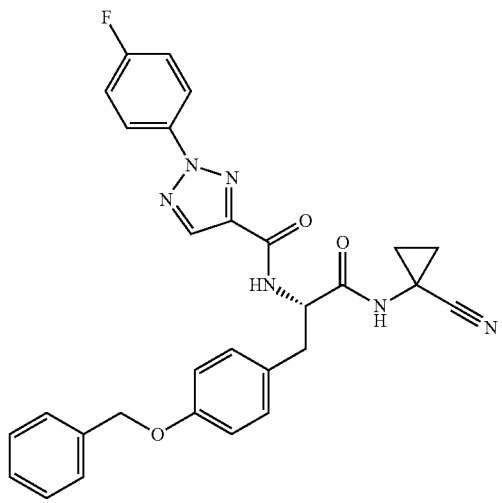 [SMILES: N#CC1(NC(=O)[C@H](Cc2ccc(OCc3ccccc3)cc2)NC(=O)c2cnn(-c3ccc(F)cc3)n2)CC1]

Example 31 was prepared from 2-(4-fluorophenyl)-2H-1,2,3-triazole-4-carboxylic acid and (S)-3-(4-(benzyloxy)phenyl)-2-((tert-butoxycarbonyl)amino)propanoic acid (CAS: 2130-96-3) in analogy to the methods described in examples 1b-d) to yield the title compound as a white solid (250 mg; 64%). MS (ESI): m/z=523.4 [M–H]$^-$.

Example 32

N-[(2S)-1-[(1-cyanocyclopropyl)amino]-4-methyl-1-oxopentan-2-yl]-2-(4-fluorophenyl)triazole-4-carboxamide

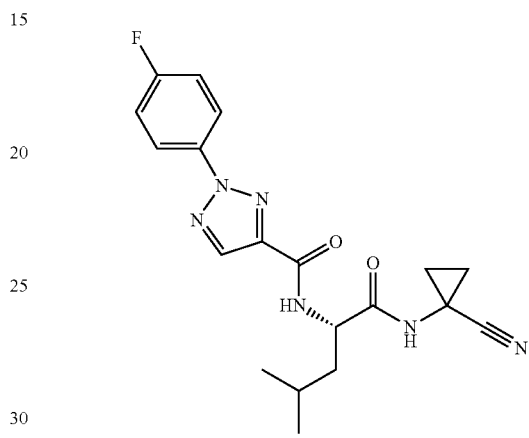

Example 32 was prepared from 2-(4-fluorophenyl)-2H-1,2,3-triazole-4-carboxylic acid and (S)-2-((tert-butoxycarbonyl)amino)-4-methylpentanoic acid (CAS: 13139-15-6) in analogy to the methods described in examples 1b-d) to yield the title compound as a white foam (100 mg; 56%). MS (ESI): m/z=385.3 [M+H]$^+$.

Example 33

N-[(2S)-3-[3-chloro-4-(trifluoromethoxy)phenyl]-1-[(1-cyanocyclopropyl)amino]-1-oxopropan-2-yl]-2-propan-2-yltriazole-4-carboxamide a) ethyl 2-isopropyl-2H-1,2,3-triazole-4-carboxylate

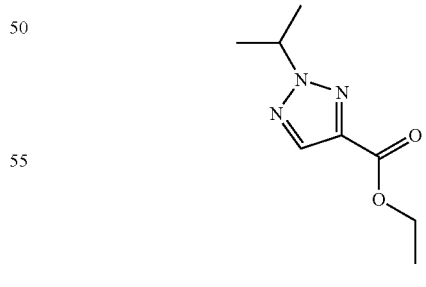

A solution of ethyl 1H-1,2,3-triazole-5-carboxylate (example 23a; 500 mg, 3.54 mmol, Eq: 1) in CAN (20 ml) was treated with 2-iodopropane (602 mg, 354 µl, 3.54 mmol, Eq: 1) and K$_2$CO$_3$ (979 mg, 7.09 mmol, Eq: 2), under Ar. The resulting mixture was stirred for 18 h at 50° C., before being filtered through celite, and concentrated. MPLC (SiO$_2$; heptane/EtOAc, gradient from 100:0 to 50:50 within 30 min) gave the title compound (157 mg, 24%) as a colorless oil. MS (ESI): m/z=184.1 [M+H]$^+$.

b) N-[(2S)-3-[3-chloro-4-(trifluoromethoxy)phenyl]-1-[(1-cyanocyclopropyl)amino]-1-oxopropan-2-yl]-2-propan-2-yltriazole-4-carboxamide

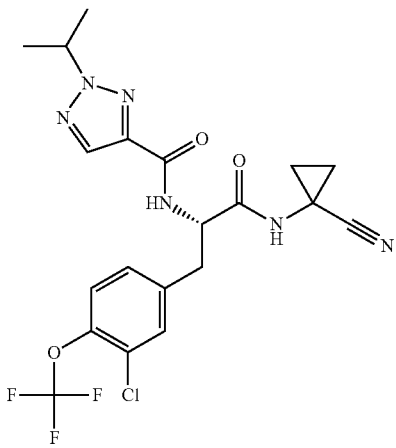 [SMILES: CC(C)n1ncc(C(=O)N[C@@H](Cc2ccc(OC(F)(F)F)c(Cl)c2)C(=O)NC2(C#N)CC2)n1]

Example 33b was prepared from ethyl 2-isopropyl-2H-1,2,3-triazole-4-carboxylate and (S)-2-amino-3-(3-chloro-4-(trifluoromethoxy)phenyl)propanoic acid hydrochloride in analogy to the methods described in examples 23c-d to yield the title compound as a light yellow foam (80 mg; 26%). MS (ESI): m/z=485.3 [M+H]$^+$.

Example 34

N-[(2S)-3-[3-chloro-4-(trifluoromethoxy)phenyl]-1-[(1-cyanocyclopropyl)amino]-1-oxopropan-2-yl]-2-methyltriazole-4-carboxamide

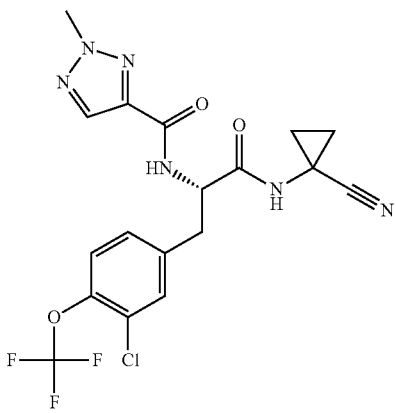 [SMILES: Cn1ncc(C(=O)N[C@@H](Cc2ccc(OC(F)(F)F)c(Cl)c2)C(=O)NC2(C#N)CC2)n1]

Example 34 was prepared from methyl iodide and (S)-2-amino-3-(3-chloro-4-(trifluoromethoxy)phenyl)propanoic acid hydrochloride in analogy to the methods described in examples 33a-b to yield the title compound as a white foam (88 mg; 31%). MS (ESI): m/z=457.2 [M+H]$^+$.

Example 35

2-(4-bromophenyl)-N-[(2S)-3-[3-chloro-4-(trifluoromethoxy)phenyl]-1-[(1-cyanocyclopropyl)amino]-1-oxopropan-2-yl]triazole-4-carboxamide a) ethyl 2-(4-bromophenyl)triazole-4-carboxylate

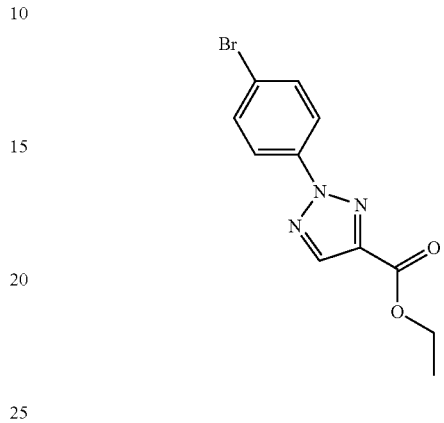

A solution of ethyl 1H-1,2,3-triazole-5-carboxylate (example 23a; 500 mg, 3.54 mmol, Eq: 1) and (4-bromophenyl)boronic acid (1.07 g, 5.31 mmol, Eq: 1.5) in CH$_2$Cl$_2$ (30 mL) was treated with copper (II) acetate (322 mg, 1.77 mmol, Eq: 0.5) and KOtBu (596 mg, 5.31 mmol, Eq: 1.5), at 25° C. under Air. The mixture was stirred at this temperature for 72 h, before being diluted with CH$_2$Cl$_2$. The organic phase was washed with water (1×), dried over Na$_2$SO$_4$, filtered and evaporated. MPLC (SiO$_2$; heptane/EtOAc, gradient from 100:0 to 0:100 within 40 min) gave the title compound (82 mg, 8%) as a white solid. MS (ESI): m/z=298.0 [M+H]$^+$.

b) 2-(4-bromophenyl)-N-[(2S)-3-[3-chloro-4-(trifluoromethoxy)phenyl]-1-[(1-cyanocyclopropyl)amino]-1-oxopropan-2-yl]triazole-4-carboxamide

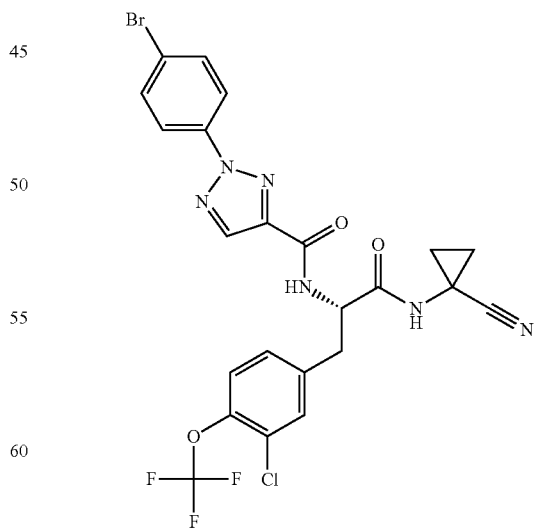

Example 35b was prepared from ethyl 2-(4-bromophenyl)triazole-4-carboxylate and (S)-2-amino-3-(3-chloro-4-(trifluoromethoxy)phenyl)propanoic acid hydrochloride in analogy to the methods described in examples 23c-d to yield the title compound as a white solid (22 mg; 25%). MS (ESI): m/z=599.2 [M+H]+.

Example 36

N-[(2S)-3-[3-chloro-4-(2-methoxyethoxy)phenyl]-1-[(1-cyanocyclopropyl)amino]-1-oxopropan-2-yl]-2-(4-fluorophenyl)triazole-4-carboxamide

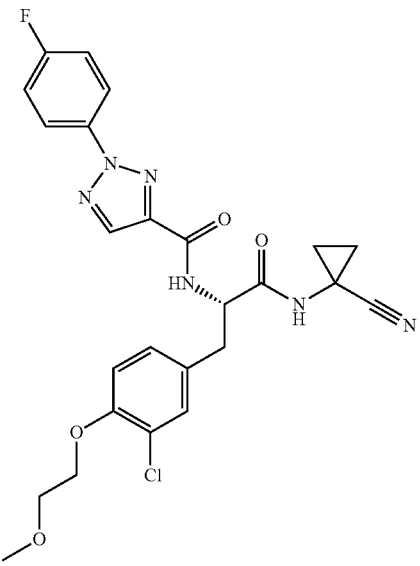 [SMILES: COCCOc1ccc(C[C@H](NC(=O)c2cnn(-c3ccc(F)cc3)n2)C(=O)NC2(C#N)CC2)cc1Cl]

Example 36 was prepared from 2-(4-fluorophenyl)-2H-1,2,3-triazole-4-carboxylic acid and dicyclohexylamine (S)-2-((tert-butoxycarbonyl)amino)-3-(3-chloro-4-hydroxyphenyl)propanoate in analogy to the methods described in examples 28a-c to yield the title compound as a white solid (57 mg; 52%). MS (ESI): m/z=525.4 [M−H]−.

Example 37

2-tert-butyl-N-[(2S)-3-[3-chloro-4-(trifluoromethoxy)phenyl]-1-[(1-cyanocyclopropyl)amino]-1-oxopropan-2-yl]triazole-4-carboxamide a) ethyl 2-tert-butyltriazole-4-carboxylate

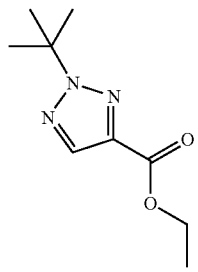

A solution of ethyl 1H-1,2,3-triazole-5-carboxylate (example 23a; 500 mg, 3.54 mmol, Eq: 1) in TFA (4.44 g, 3 ml, 39 mmol, Eq: 11) was treated with 2-methylpropan-2-ol (525 mg, 673 μl, 7.09 mmol, Eq: 2) and H$_2$SO$_4$ (347 mg, 189 μl, 3.54 mmol, Eq: 1), at 25° C. The resulting mixture was stirred for 5 h at this temperature, before being partitioned between H$_2$O and EtOAc. The organic phase was washed with sat. NaHCO$_3$, brine, dried over Na$_2$SO$_4$, filtered, and evaporated. MPLC (SiO$_2$; heptane/EtOAc, gradient from 100:0 to 50:50 within 30 min) gave the title compound (313 mg, 45%) as a colorless oil. MS (ESI): m/z=198.1 [M+H]+.

b) 2-tert-butyl-N-[(2S)-3-[3-chloro-4-(trifluoromethoxy)phenyl]-1-[(1-cyanocyclopropyl)amino]-1-oxopropan-2-yl]triazole-4-carboxamide

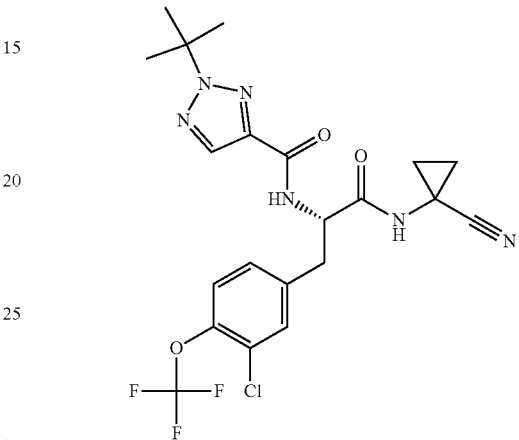

Example 37b was prepared from ethyl 2-tert-butyltriazole-4-carboxylate and (S)-2-amino-3-(3-chloro-4-(trifluoromethoxy)phenyl)propanoic acid hydrochloride in analogy to the methods described in examples 23c-d to yield the title compound as a white foam (148 mg; 50%). MS (ESI): m/z=499.3 [M+H]+.

Example 38

N-[(2S)-3-[3-chloro-4-(cyclobutylmethoxy)phenyl]-1-[(1-cyanocyclopropyl)amino]-1-oxopropan-2-yl]-2-(4-fluorophenyl)triazole-4-carboxamide

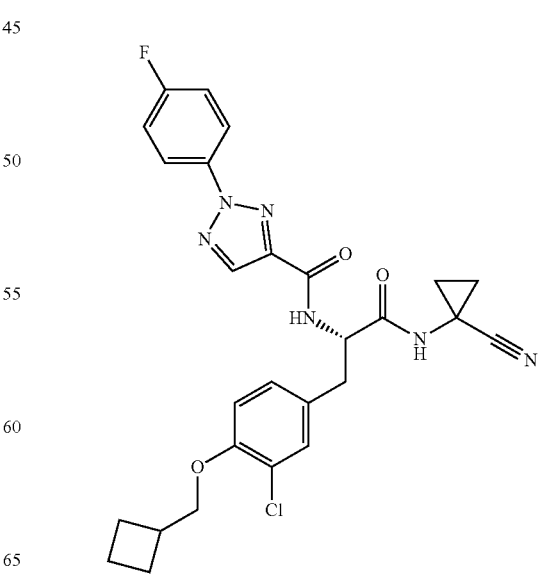

Example 38 was prepared from 2-(4-fluorophenyl)-2H-1,2,3-triazole-4-carboxylic acid and dicyclohexylamine (S)-2-((tert-butoxycarbonyl)amino)-3-(3-chloro-4-hydroxyphenyl)propanoate in analogy to the methods described in examples 28a-c to yield the title compound as a yellow foam (51 mg; 37%). MS (ESI): m/z=537.2 [M+H]⁺.

Example 39

N-[(2S)-1-[(1-cyanocyclopropyl)amino]-1-oxo-3-pyridin-4-ylpropan-2-yl]-2-(4-fluorophenyl)triazole-4-carboxamide a) 9H-fluoren-9-ylmethyl N-[(2S)-1-[(1-cyanocyclopropyl)amino]-1-oxo-3-pyridin-4-ylpropan-2-yl]carbamate

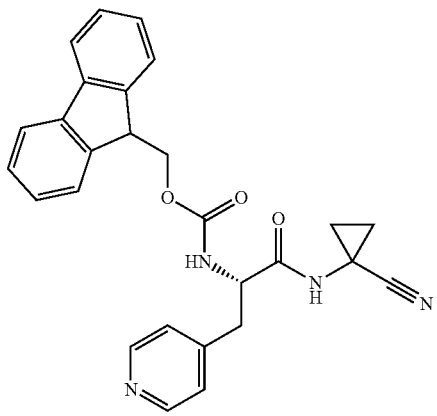 [SMILES: N#CC1(NC(=O)[C@H](Cc2ccncc2)NC(=O)OCC2c3ccccc3-c3ccccc32)CC1]

Example 39a was prepared from (S)-2-((((9H-fluoren-9-yl)methoxy)carbonyl)amino)-3-(pyridin-4-yl)propanoic acid and 1-aminocyclopropanecarbonitrile hydrochloride in analogy to the method described in example 1b to yield the title compound as a white solid (140 mg; 60%). MS (ESI): m/z=453.3 [M+H]⁺.

b) (2S)-2-amino-N-(1-cyanocyclopropyl)-3-pyridin-4-ylpropanamide

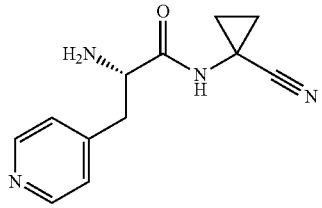 [SMILES: N#CC1(NC(=O)[C@@H](N)Cc2ccncc2)CC1]

A solution of (S)-(9H-fluoren-9-yl)methyl (1-((1-cyanocyclopropyl)amino)-1-oxo-3-(pyridin-4-yl)propan-2-yl)carbamate (example 39a; 120 mg, 265 mol, Eq: 1) in CH₂Cl₂ (5 ml) was treated with piperidine (645 mg, 750 µl, 7.58 mmol, Eq: 28.6), at 23° C., under Ar. The resulting mixture was stirred for 4 h at this temperature. After that, the mixture was evaporated to dryness. The crude product was purified by flash chromatography (SiO₂; CH₂Cl₂/MeOH, gradient from 100:0 to 90:10 within 30 min) to yield the title compound (36 mg, 59%) as a colorless oil. MS (ESI): m/z=231.2 [M+H]⁺.

c) N-[(2S)-1-[(1-cyanocyclopropyl)amino]-1-oxo-3-pyridin-4-ylpropan-2-yl]-2-(4-fluorophenyl)triazole-4-carboxamide

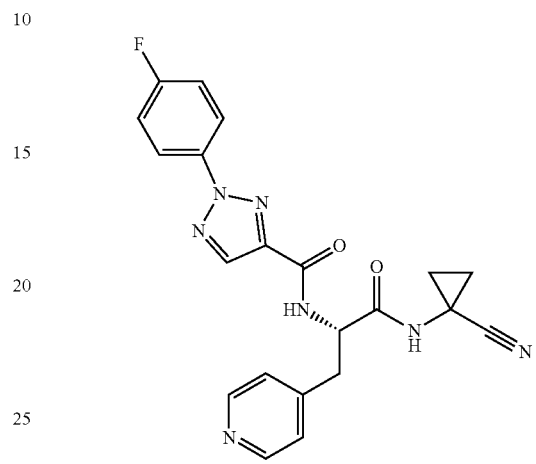

Example 39c was prepared from 2-(4-fluorophenyl)-2H-1,2,3-triazole-4-carboxylic acid and (2S)-2-amino-N-(1-cyanocyclopropyl)-3-pyridin-4-ylpropanamide (example 39b) in analogy to the method described in example 1d to yield the title compound as a white solid (53 mg; 81%). MS (ESI): m/z=420.2 [M+H]⁺.

Example 40

N-[(2S)-3-(4-chlorophenyl)-1-[(1-cyanocyclopropyl)amino]-1-oxopropan-2-yl]-2-(4-fluorophenyl)triazole-4-carboxamide

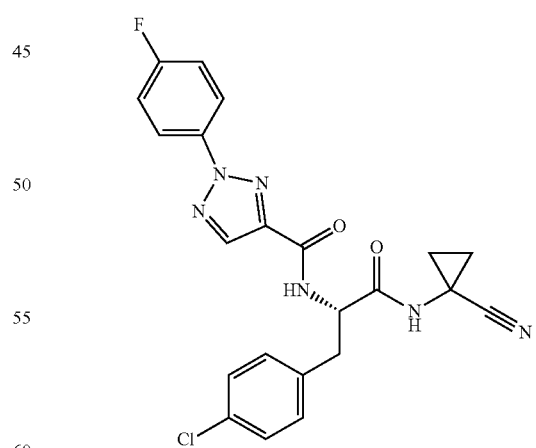

Example 40 was prepared from 2-(4-fluorophenyl)-2H-1,2,3-triazole-4-carboxylic acid and (S)-2-((tert-butoxycarbonyl)amino)-3-(4-chlorophenyl)propanoic acid (CAS: 68090-88-0) in analogy to the methods described in examples 1b-d) to yield the title compound as a white solid (220 mg; 72%). MS (ESI): m/z=451.4 [M−H]⁻.

Example 41

N-[(2S)-3-[3-chloro-4-(trifluoromethoxy)phenyl]-1-[(1-cyanocyclopropyl)amino]-1-oxopropan-2-yl]-2-pyridin-4-yltriazole-4-carboxamide

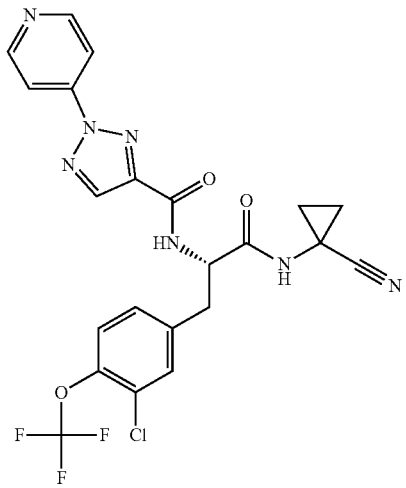 [SMILES: N#CC1(NC(=O)[C@H](Cc2ccc(OC(F)(F)F)c(Cl)c2)NC(=O)c2cnn(-c3ccncc3)n2)CC1]

Example 41 was prepared from pyridine-4-boronic acid and (S)-2-amino-3-(3-chloro-4-(trifluoromethoxy)phenyl) propanoic acid hydrochloride in analogy to the methods described in examples 35a-b to yield the title compound as a white solid (49 mg; 60%). MS (ESI): m/z=520.0 [M+H]$^+$.

Example 42

N-[(2S)-3-[3-chloro-4-(trifluoromethoxy)phenyl]-1-[(1-cyanocyclopropyl)amino]-1-oxopropan-2-yl]-2-cyclobutyltriazole-4-carboxamide a) ethyl 2-cyclobutyltriazole-4-carboxylate

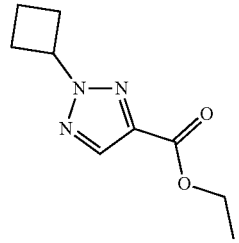

A solution of ethyl 1H-1,2,3-triazole-5-carboxylate (example 23a; 300 mg, 2.13 mmol, Eq: 1) in toluene (15 ml) was treated with cyclobutanol (230 mg, 250 µl, 3.19 mmol, Eq: 1.5) and 2-(tributylphosphoranylidene)acetonitrile (1.03 g, 1.11 ml, 4.25 mmol, Eq: 2), under Ar. The mixture was stirred for 1 h 30 at 80° C., before being diluted with EtOAc. The organic phase was washed with water (1×) and brine (2×), dried over Na$_2$SO$_4$, filtered, and evaporated. MPLC (SiO$_2$; heptane/EtOAc, gradient from 100:0 to 70:30 within 30 min) gave the title compound (142 mg, 33.9%) as a colorless oil. MS (ESI): m/z=196.1 [M+H]$^+$.

b) N-[(2S)-3-[3-chloro-4-(trifluoromethoxy)phenyl]-1-[(1-cyanocyclopropyl)amino]-1-oxopropan-2-yl]-2-cyclobutyltriazole-4-carboxamide

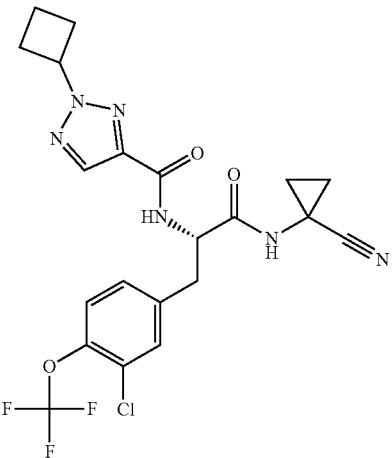 [SMILES: N#CC1(NC(=O)[C@H](Cc2ccc(OC(F)(F)F)c(Cl)c2)NC(=O)c2cnn(C3CCC3)n2)CC1]

Example 42b was prepared from ethyl 2-cyclobutyltriazole-4-carboxylate (example 42a) and (S)-2-amino-3-(3-chloro-4-(trifluoromethoxy)phenyl)propanoic acid hydrochloride in analogy to the methods described in examples 23c-d to yield the title compound as a white foam (76 mg; 51%). MS (ESI): m/z=497.2 [M+H]$^+$.

Example 43

N-[(2S)-3-(3-chloro-4-cyanophenyl)-1-[(1-cyanocyclopropyl)amino]-1-oxopropan-2-yl]-2-(4-fluorophenyl)triazole-4-carboxamide

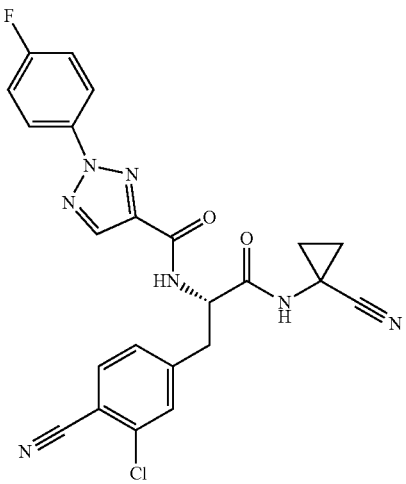 [SMILES: N#Cc1ccc(C[C@H](NC(=O)c2cnn(-c3ccc(F)cc3)n2)C(=O)NC2(C#N)CC2)cc1Cl]

Example 43 was prepared from 2-(4-fluorophenyl)-2H-1,2,3-triazole-4-carboxylic acid and (S)-2-amino-3-(3-chloro-4-cyanophenyl)propanoic acid hydrochloride in analogy to the methods described in examples 1a-d) to yield the title compound as a white solid (102 mg; 94%). MS (ESI): m/z=478.2 [M+H]$^+$.

Example 44

N-[(2S)-3-[3-chloro-4-(trifluoromethoxy)phenyl]-1-[(1-cyanocyclopropyl)amino]-1-oxopropan-2-yl]-2-(oxan-4-yl)triazole-4-carboxamide

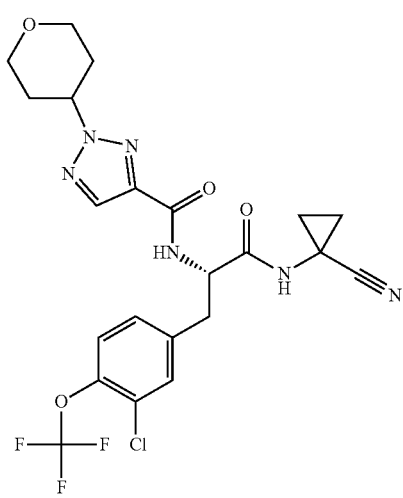 [SMILES: N#CC1(NC(=O)[C@H](Cc2ccc(OC(F)(F)F)c(Cl)c2)NC(=O)c2cnn(C3CCOCC3)n2)CC1]

Example 44 was prepared from tetrahydro-2H-pyran-4-ol and (S)-2-amino-3-(3-chloro-4-(trifluoromethoxy)phenyl) propanoic acid hydrochloride in analogy to the methods described in example 42 to yield the title compound as a white foam (53 mg; 40%). MS (ESI): m/z=527.3 [M+H]$^+$.

Example 45

N-[(2S)-1-[(1-cyanocyclopropyl)amino]-3-(3,4-dichlorophenyl)-1-oxopropan-2-yl]-2-(oxan-4-yl)triazole-4-carboxamide

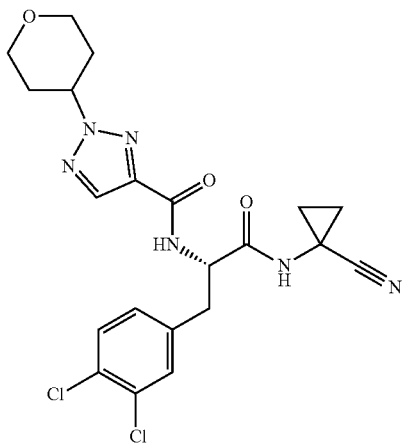 [SMILES: N#CC1(NC(=O)[C@H](Cc2ccc(Cl)c(Cl)c2)NC(=O)c2cnn(C3CCOCC3)n2)CC1]

Example 45 was prepared from tetrahydro-2H-pyran-4-ol and (S)-2-amino-3-(3,4-dichlorophenyl)propanoic acid (CAS: 52794-99-7) in analogy to the methods described in example 42 to yield the title compound as a white foam (46 mg; 38%). MS (ESI): m/z=478.2 [M+H]$^+$.

Example 46

N-[(2S)-3-[3-chloro-4-(trifluoromethoxy)phenyl]-1-[(1-cyanocyclopropyl)amino]-1-oxopropan-2-yl]-2-cyclohexyltriazole-4-carboxamide

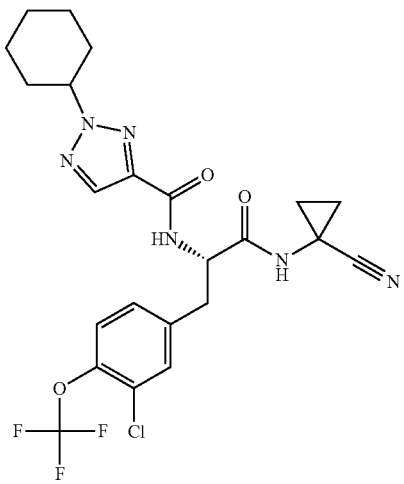 [SMILES: N#CC1(NC(=O)[C@H](Cc2ccc(OC(F)(F)F)c(Cl)c2)NC(=O)c2cnn(C3CCCCC3)n2)CC1]

Example 46 was prepared from cyclohexanol (CAS: 108-93-0) and (S)-2-amino-3-(3-chloro-4-(trifluoromethoxy)phenyl)propanoic acid hydrochloride in analogy to the methods described in example 42 to yield the title compound as a white foam (50 mg; 47%). MS (ESI): m/z=525.2 [M+H]$^+$.

Example 47

N-[(2S)-1-[(1-cyanocyclopropyl)amino]-3-(2-cyanophenyl)-1-oxopropan-2-yl]-2-(4-fluorophenyl)triazole-4-carboxamide

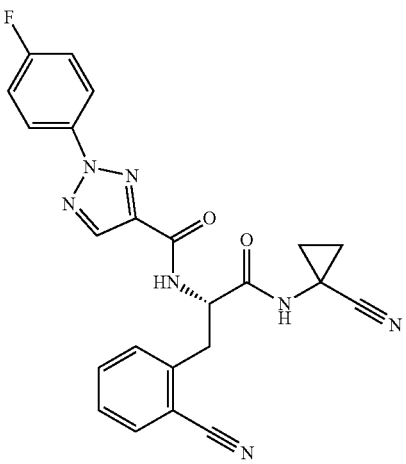 [SMILES: N#Cc1ccccc1C[C@H](NC(=O)c1cnn(-c2ccc(F)cc2)n1)C(=O)NC1(C#N)CC1]

Example 47 was prepared from 2-(4-fluorophenyl)-2H-1,2,3-triazole-4-carboxylic acid and (S)-2-((tert-butoxycarbonyl)amino)-3-(2-cyanophenyl)propanoic acid (CAS: 216312-53-7) in analogy to the methods described in examples 1b-d) to yield the title compound as a white solid (163 mg; 77%). MS (ESI): m/z=444.2 [M+H]$^+$.

Example 48

N-[(2S)-1-[(1-cyanocyclopropyl)amino]-1-oxo-3-[2-(trifluoromethyl)phenyl]propan-2-yl]-2-(4-fluorophenyl)triazole-4-carboxamide

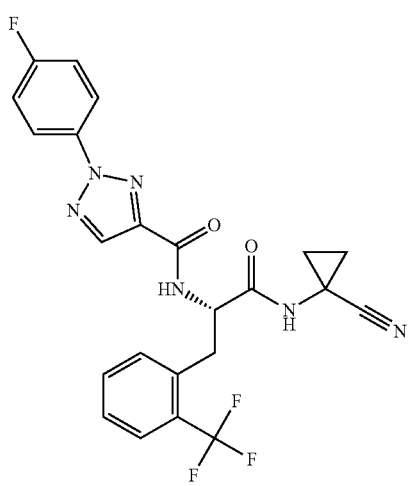 [SMILES: N#CC1(NC(=O)[C@H](Cc2ccccc2C(F)(F)F)NC(=O)c2cnn(-c3ccc(F)cc3)n2)CC1]

Example 48 was prepared from 2-(4-fluorophenyl)-2H-1,2,3-triazole-4-carboxylic acid and (S)-2-amino-3-(2-(trifluoromethyl)phenyl)propanoic acid (CAS: 119009-47-1) in analogy to the methods described in examples 1a-d) to yield the title compound as a white solid (57 mg; 18%). MS (ESI): m/z=487.2 [M+H]⁺.

Example 49

N-[(2S)-3-(2-chlorophenyl)-1-[(1-cyanocyclopropyl)amino]-1-oxopropan-2-yl]-2-(4-fluorophenyl)triazole-4-carboxamide

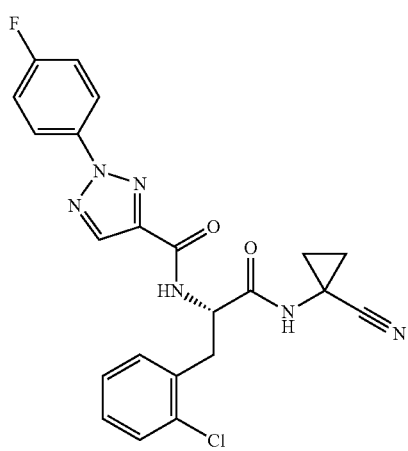 [SMILES: N#CC1(NC(=O)[C@H](Cc2ccccc2Cl)NC(=O)c2cnn(-c3ccc(F)cc3)n2)CC1]

Example 49 was prepared from 2-(4-fluorophenyl)-2H-1,2,3-triazole-4-carboxylic acid and (S)-2-amino-3-(2-chlorophenyl)propanoic acid (CAS: 103616-89-3) in analogy to the methods described in examples 1a-d) to yield the title compound as a white solid (82 mg; 48%). MS (ESI): m/z=453.2 [M+H]⁺.

Example 50

N-[(2S)-1-[(1-cyanocyclopropyl)amino]-3-(3,4-dichlorophenyl)-1-oxopropan-2-yl]-2-(3,3-difluorocyclobutyl)triazole-4-carboxamide

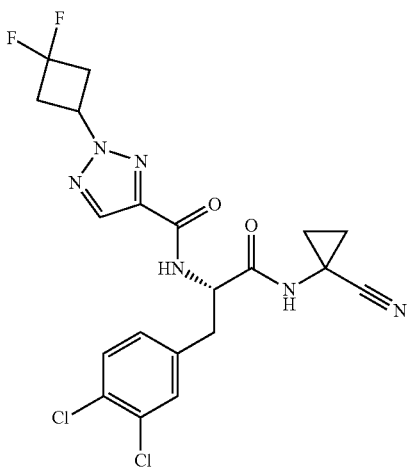 [SMILES: N#CC1(NC(=O)[C@H](Cc2ccc(Cl)c(Cl)c2)NC(=O)c2cnn(C3CC(F)(F)C3)n2)CC1]

Example 50 was prepared from 3,3-difluorocyclobutanol and (S)-2-amino-3-(3,4-dichlorophenyl)propanoic acid) (CAS: 52794-99-7) in analogy to the methods described in example 42 to yield the title compound as a white solid (60 mg; 56%). MS (ESI): m/z=483.1 [M+H]⁺.

Example 51 tert-butyl 6-[4-[[(2S)-3-[3-chloro-4-(trifluoromethoxy)phenyl]-1-[(1-cyanocyclopropyl)amino]-1-oxopropan-2-yl]carbamoyl]triazol-2-yl]-2-azaspiro[3.3]heptane-2-carboxylate

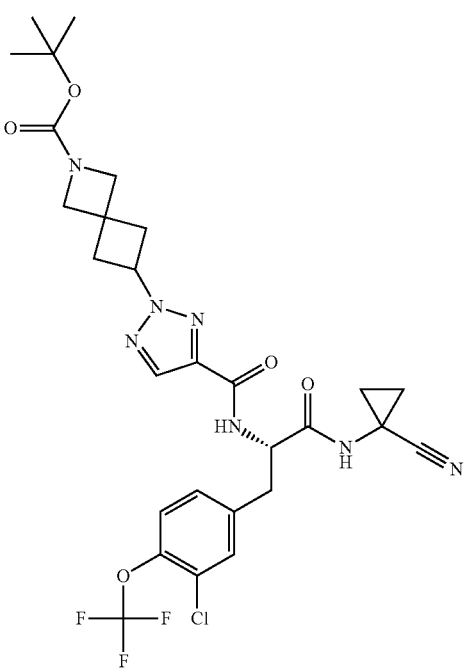 [SMILES: CC(C)(C)OC(=O)N1CC2(CC(n3ncc(C(=O)N[C@@H](Cc4ccc(OC(F)(F)F)c(Cl)c4)C(=O)NC4(C#N)CC4)n3)C2)C1]

Example 51 was prepared from tert-butyl 6-hydroxy-2-azaspiro[3.3]heptane-2-carboxylate (CAS: 1147557-97-8) and (S)-2-amino-3-(3-chloro-4-(trifluoromethoxy)phenyl) propanoic acid hydrochloride in analogy to the methods described in example 42 to yield the title compound as an off-white foam (115 mg; 52%). MS (ESI): m/z=637.4 [M−H]⁻.

Example 52

N-[(2S)-1-[(1-cyanocyclopropyl)amino]-3-(3,4-dichlorophenyl)-1-oxopropan-2-yl]-2-cyclobutyltriazole-4-carboxamide

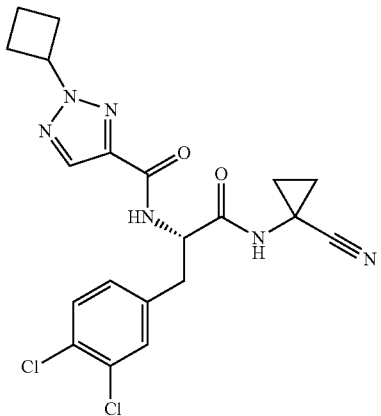 [SMILES: N#CC1(NC(=O)[C@H](Cc2ccc(Cl)c(Cl)c2)NC(=O)c2cnn(C3CCC3)n2)CC1]

Example 52 was prepared from cyclobutanol and (S)-2-amino-3-(3,4-dichlorophenyl)propanoic acid) (CAS: 52794-99-7) in analogy to the methods described in example 42 to yield the title compound as a white foam (43 mg; 32%). MS (ESI): m/z=445.2 [M−H]⁻.

Example 53

N-[(2S)-3-[3-chloro-4-(trifluoromethoxy)phenyl]-1-[(1-cyanocyclopropyl)amino]-1-oxopropan-2-yl]-2-(3,3-difluorocyclobutyl)triazole-4-carboxamide

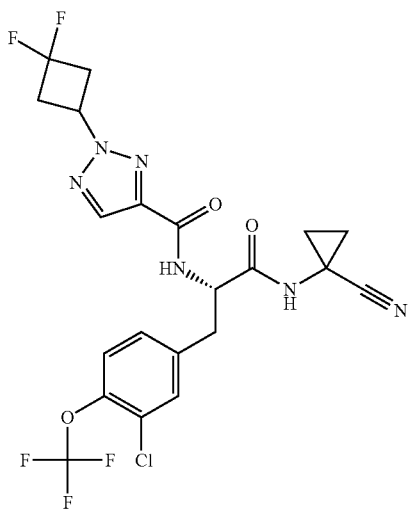 [SMILES: N#CC1(NC(=O)[C@H](Cc2ccc(OC(F)(F)F)c(Cl)c2)NC(=O)c2cnn(C3CC(F)(F)C3)n2)CC1]

Example 53 was prepared from 3,3-difluorocyclobutanol and (S)-2-amino-3-(3-chloro-4-(trifluoromethoxy)phenyl) propanoic acid hydrochloride in analogy to the methods described in example 42 to yield the title compound as a white solid (47 mg; 40%). MS (ESI): m/z=531.2 [M−H]⁻.

Example 54

N-[(2S)-1-[(1-cyanocyclopropyl)amino]-3-(3,4-dichlorophenyl)-1-oxopropan-2-yl]-2-(oxetan-3-yl)triazole-4-carboxamide

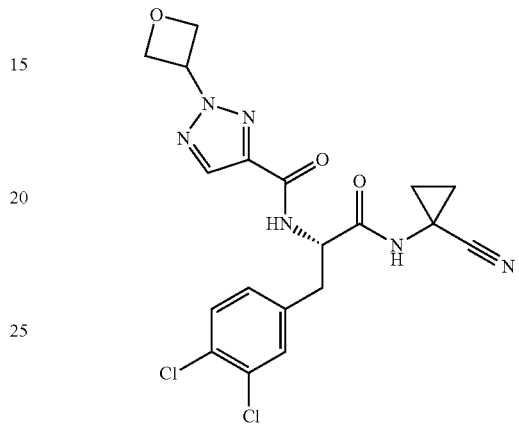

Example 54 was prepared from oxetan-3-ol and (S)-2-amino-3-(3,4-dichlorophenyl)propanoic acid) (CAS: 52794-99-7) in analogy to the methods described in example 42 to yield the title compound as a white solid (56 mg; 47%). MS (ESI): m/z=447.2 [M−H]⁻.

Example 55

N-[(2S)-3-[3-chloro-4-(trifluoromethoxy)phenyl]-1-[(1-cyanocyclopropyl)amino]-1-oxopropan-2-yl]-2-(oxetan-3-yl)triazole-4-carboxamide

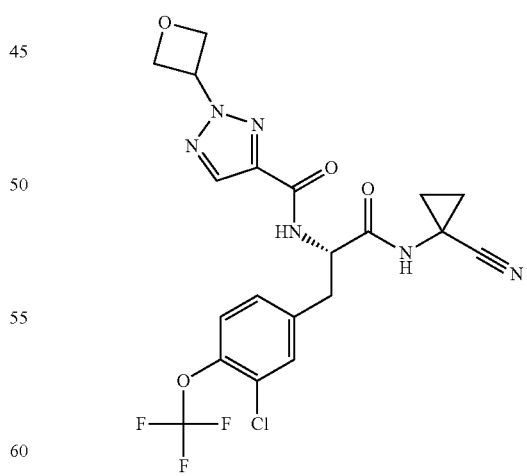

Example 55 was prepared from oxetan-3-ol and (S)-2-amino-3-(3-chloro-4-(trifluoromethoxy)phenyl)propanoic acid hydrochloride in analogy to the methods described in example 42 to yield the title compound as a white solid (55 mg; 41%). MS (ESI): m/z=497.2 [M−H]⁻.

Example 56

2-(2-azaspiro[3.3]heptan-6-yl)-N-[(2S)-3-[3-chloro-4-(trifluoromethoxy)phenyl]-1-[(1-cyanocyclopropyl)amino]-1-oxopropan-2-yl]triazole-4-carboxamide

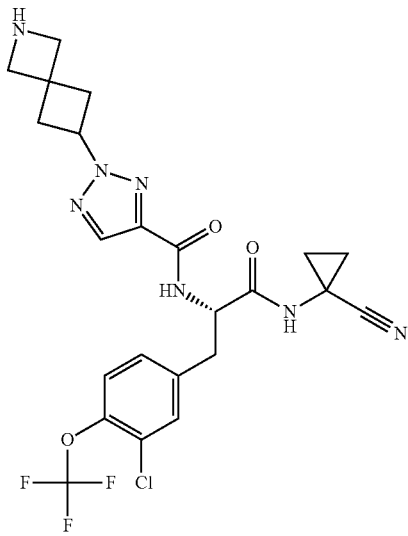 [SMILES: N#CC1(NC(=O)[C@H](Cc2ccc(OC(F)(F)F)c(Cl)c2)NC(=O)c2cnn(C3CC4(CNC4)C3)n2)CC1]

A solution of (S)-tert-butyl 6-(4-((3-(3-chloro-4-(trifluoromethoxy)phenyl)-1-((1-cyanocyclopropyl)amino)-1-oxopropan-2-yl)carbamoyl)-2H-1,2,3-triazol-2-yl)-2-azaspiro[3.3]heptane-2-carboxylate (example 51; 72 mg, 113 µmol, Eq: 1) in formic acid (519 mg, 433 µl, 11.3 mmol, Eq: 100) was stirred at 25° C. for 1 h, before being diluted with 5 mL of water and extracted with CH₂Cl₂ (1×). The aqueous phase was then basified to pH=9 with 2N NaOH and then NaOH pellets, and the aqueous phase was extracted with CH₂Cl₂ (3×), dried over Na₂SO₄, filtered, and evaporated. RP-HPLC gave the title compound (24 mg, 40%) as a light yellow solid. MS (ESI): m/z=538.2 [M+H]⁺.

Example 57 tert-butyl 3-[4-[[(2S)-3-[3-chloro-4-(trifluoromethoxy)phenyl]-1-[(1-cyanocyclopropyl)amino]-1-oxopropan-2-yl]carbamoyl]triazol-2-yl]pyrrolidine-1-carboxylate

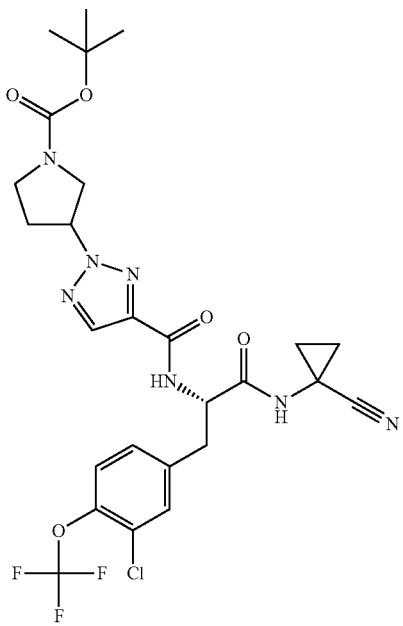 [SMILES: CC(C)(C)OC(=O)N1CCC(n2ncc(C(=O)N[C@@H](Cc3ccc(OC(F)(F)F)c(Cl)c3)C(=O)NC3(C#N)CC3)n2)C1]

Example 57 was prepared from tert-butyl 3-hydroxypyrrolidine-1-carboxylate and (S)-2-amino-3-(3-chloro-4-(trifluoromethoxy)phenyl)propanoic acid hydrochloride in analogy to the methods described in example 42 to yield the title compound as a white foam (68 mg; 55%). MS (ESI): m/z=634.2 [M+Na]⁺.

Example 58

N-[(2S)-3-[3-chloro-4-(trifluoromethoxy)phenyl]-1-[(1-cyanocyclopropyl)amino]-1-oxopropan-2-yl]-2-pyrrolidin-3-yltriazole-4-carboxamide

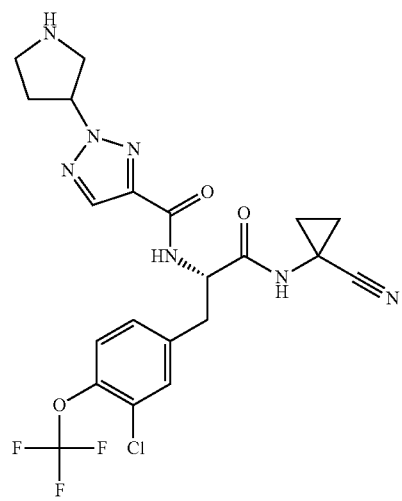 [SMILES: N#CC1(NC(=O)[C@H](Cc2ccc(OC(F)(F)F)c(Cl)c2)NC(=O)c2cnn(C3CCNC3)n2)CC1]

Example 58 was prepared from tert-butyl 3-[4-[[(2S)-3-[3-chloro-4-(trifluoromethoxy)phenyl]-1-[(1-cyanocyclopropyl)amino]-1-oxopropan-2-yl]carbamoyl]triazol-2-yl]pyrrolidine-1-carboxylate (example 57) in analogy to the method described in example 56 to yield the title compound as a light yellow waxy solid (32 mg; 77%). MS (ESI): m/z=512.2 [M+H]⁺.

Example 59

2-(azetidin-3-yl)-N-[(2S)-3-[3-chloro-4-(trifluoromethoxy)phenyl]-1-[(1-cyanocyclopropyl)amino]-1-oxopropan-2-yl]triazole-4-carboxamide

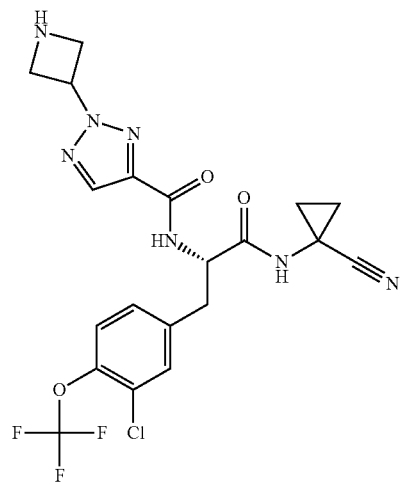 [SMILES: N#CC1(NC(=O)[C@H](Cc2ccc(OC(F)(F)F)c(Cl)c2)NC(=O)c2cnn(C3CNC3)n2)CC1]

Example 59 was prepared from tert-butyl 3-hydroxyazetidine-1-carboxylate and (S)-2-amino-3-(3-chloro-4-(trifluoromethoxy)phenyl)propanoic acid hydrochloride in analogy to the methods described in example 56 to yield the title compound as a light yellow oil (14 mg; 22%). MS (ESI): m/z=498.2 [M+H]$^+$.

Example 60

N-[(2S)-1-[(1-cyanocyclopropyl)amino]-1-oxo-3-pyridin-2-ylpropan-2-yl]-2-(4-fluorophenyl)triazole-4-carboxamide

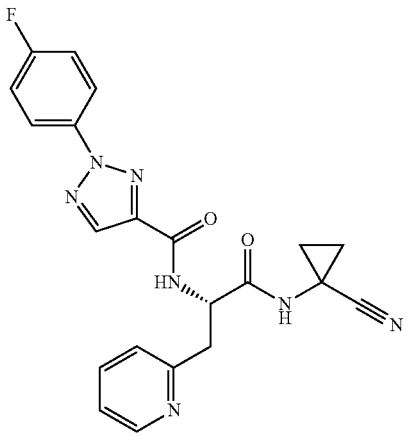 [SMILES: N#CC1(NC(=O)[C@H](Cc2ccccn2)NC(=O)c2cnn(-c3ccc(F)cc3)n2)CC1]

Example 60 was prepared from 2-(4-fluorophenyl)-2H-1,2,3-triazole-4-carboxylic acid and (S)-2-((tert-butoxycarbonyl)amino)-3-(pyridin-2-yl)propanoic acid (CAS: 71239-85-5) in analogy to the methods described in examples 1b-d) to yield the title compound as a white solid (37 mg; 60%). MS (ESI): m/z=420.2 [M+H]$^+$.

Example 61

Pharmacological Tests

Activity Against *Trypanosoma brucei* Rhodesiense STIB900

This stock was isolated in 1982 from a human patient in Tanzania and after several mouse passages cloned and adapted to axenic culture conditions (Baltz, T., D. Baltz, C. Giroud, and J. Crockett. 1985, Cultivation in a semi-defined medium of animal infective forms of *Trypanosoma brucei, T. equiperdum, T. evansi, T. rhodesiense* and *T. gambiense*. EMBO Journal 4:1273-1277). Minimum Essential Medium (50 µl) supplemented with 25 mM HEPES, 1 g/l additional glucose, 1% MEM non-essential amino acids (100×), 0.2 mM 2-mercaptoethanol, 1 mM Na-pyruvate and 15% heat inactivated horse serum was added to each well of a 96-well microtiter plate. Serial drug dilutions of eleven 3-fold dilution steps covering a range from 100 to 0.002 m/ml were prepared. Then 4×10$^3$ bloodstream forms of *T. b. rhodesiense* STIB 900 in 50 µl was added to each well and the plate incubated at 37° C. under a 5% CO$_2$ atmosphere for 70 h. 10 µl Alamar Blue (resazurin, 12.5 mg in 100 ml double-distilled water) was then added to each well and incubation continued for a further 2-4 h (Räz, B., M. Iten, Y. Grether-Buhler, R. Kaminsky, and R. Brun. 1997, The Alamar Blue assay to determine drug sensitivity of African trypanosomes (*T.b. rhodesiense* and *T.b. gambiense*) in vitro. Acta Trop 68:139-47). Then the plates were read with a Spectramax Gemini XS microplate fluorometer (Molecular Devices Cooperation, Sunnyvale, Calif., USA) using an excitation wave length of 536 nm and an emission wave length of 588 nm. The IC50 values were calculated by linear regression (Huber, W. Koella, J. C. 1993, A comparison of the three methods of estimating EC50 in studies of drug resistance of malaria parasites. Acta Trop. 55, 257-261) from the sigmoidal dose inhibition curves using SoftmaxPro software (Molecular Devices Cooperation, Sunnyvale, Calif., USA). Melarsoprol is used as control.

The results are given in Table 1 below.

TABLE 1

| Example | IC50 [uM] (*T. brucei rhodesiense*) |
|---|---|
| 1 | 0.003 |
| 2 | 0.005 |
| 3 | 0.071 |
| 4 | 0.005 |
| 5 | 4.43 |
| 6 | 0.05 |
| 7 | 0.02 |
| 8 | 0.068 |
| 9 | 0.009 |
| 10 | 0.013 |
| 11 | 0.278 |
| 12 | 0.162 |
| 13 | 0.003 |
| 14 | 0.145 |
| 15 | 0.005 |
| 16 | 0.005 |
| 17 | 0.413 |
| 18 | 0.007 |
| 19 | 10.07 |
| 20 | 16.15 |
| 22 | 16.55 |
| 23 | 0.067 |
| 24 | 0.022 |
| 25 | 1.33 |
| 26 | 0.001 |
| 27 | 0.516 |
| 28 | 0.19 |
| 29 | 0.007 |
| 30 | 0.005 |
| 31 | 0.019 |
| 32 | 2.23 |
| 33 | 0.004 |
| 34 | 0.04 |
| 35 | 0.028 |
| 36 | 0.065 |
| 37 | 0.004 |

The compounds of the invention have a CatS IC$_{50}$ below 5 uM. Particular compounds of the invention have a CatS IC$_{50}$ below 1 uM, in particular below 0.1 uM.

The compound of formula (I) is a preferential human Cat S inhibitor with a selectivity over human Cat K, Cat B and Cat L of at least 10 fold.

Example A

Film Coated Tablets Containing the Following Ingredients can be Manufactured in a Conventional Manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |

57
-continued

| Ingredients | Per tablet | |
|---|---|---|
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidone in water. The granulate is then mixed with sodium starch glycolate and magnesium stearate and compressed to yield kernels of 120 or 350 mg respectively. The kernels are lacquered with an aq. solution/suspension of the above mentioned film coat.

Example B

Capsules Containing the Following Ingredients can be Manufactured in a Conventional Manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection Solutions can have the Following Composition:

| Compound of formula (I) | 3.0 mg |
|---|---|
| Polyethylene glycol 400 | 150.0 mg |
| Acetic acid | q.s. ad pH 5.0 |
| Water for injection solutions | ad 1.0 ml |

The active ingredient is dissolved in a mixture of Polyethylene glycol 400 and water for injection (part). The pH is adjusted to 5.0 by addition of acetic acid. The volume is adjusted to 1.0 ml by addition of the residual amount of water. The solution is filtered, filled into vials using an appropriate overage and sterilized.

We claim:
1. A compound of formula (I)

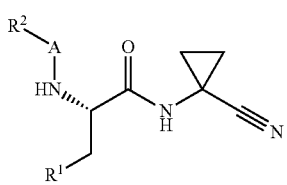

(I)

wherein
A is —C(O)— or —CHCF$_3$—;
R$^1$ is propyl, pyridinyl or R$^3$;
R$^2$ is (A), (B), (C), (D), (E), (F) or (G);

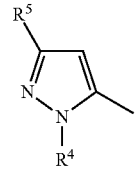

(A)

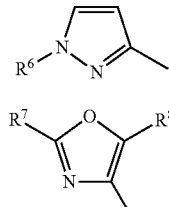

(B)

(C)

(D)

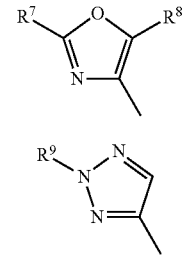

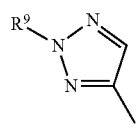

(E)

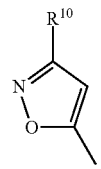

(F)

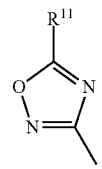

(G)

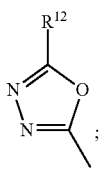

R$^3$ is (H);

(H)

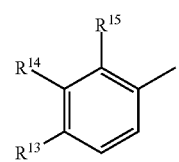

R$^4$ is hydrogen, alkyl or haloalkyl;
R$^5$ is alkyl, haloalkyl, cycloalkyl, phenyl, halophenyl or alkoxyphenyl;
R$^6$ is halophenyl;
R$^7$ is halophenyl;
R$^8$ is alkyl;

R⁹ is alkyl, cycloalkyl, halocycloalkyl, phenyl, halophenyl, alkylsulphanylphenyl, pyridinyl, halopyridinyl, oxanyl, azaspiro[3.3]heptyl, alkoxycarbonylazaspiro[3.3]heptyl, oxetanyl, pyrrolidinyl, alkoxycarbonylpyrrolidinyl, azetidinyl or alkylcarbonylazetidinyl;

R¹⁰ is phenyl;

R¹¹ is halophenyl;

R¹² is phenyl or halophenyl;

R¹³ is hydrogen, halogen, haloalkyl, haloalkoxy, cycloalkylalkoxy, phenylalkoxy, alkoxyalkoxy or cyano;

R¹⁴ is hydrogen, halogen or haloalkyl; and

R¹⁵ is hydrogen, halogen, cyano or haloalkyl;

or a pharmaceutically acceptable salt or ester thereof;

provided that N-[(1S)-1-[(3-chlorophenyl)methyl]-2-[(1-cyanocyclopropyl)amino]-2-oxoethyl]-3-(1,1-dimethylethyl)-1-methyl-1H-pyrazole-5-carboxamide is excluded.

2. The compound according to claim 1, wherein A is —C(O)—.

3. The compound according to claim 1 wherein R¹ is R³.

4. The compound according to any one of claim 1, wherein R² is (D) or (E).

5. The compound according to claim 1 wherein R⁴ is hydrogen, methyl or difluoroethyl.

6. The compound according to claim 1 wherein R⁵ is methyl, tert-butyl, trifluoromethyl, cyclopropyl, phenyl, chlorophenyl, fluorophenyl or methoxyphenyl.

7. The compound according to claim 1 wherein R⁶ is fluorophenyl.

8. The compound according to claim 1, wherein R⁷ is chlorophenyl.

9. The compound according to claim 1 wherein R⁸ is methyl.

10. The compound according to claim 1, wherein R⁹ is alkyl, phenyl, halophenyl, pyridinyl or halopyridinyl.

11. The compound according to claim 1, wherein R⁹ is methyl, propyl, tert-butyl, phenyl, fluorophenyl, chlorophenyl, pyridinyl or fluoropyridinyl.

12. The compound according to claim 1 wherein:
A is —C(O)—;
R⁴ is hydrogen, methyl or difluoroethyl;
R⁵ is methyl, tert-butyl, trifluoromethyl, cyclopropyl, phenyl, chlorophenyl, fluorophenyl or methoxyphenyl;
R⁶ is fluorophenyl;
R⁷ is chlorophenyl;
R⁸ is methyl;
R⁹ is methyl, propyl, tert-butyl, phenyl, fluorophenyl, chlorophenyl, pyridinyl or fluoropyridinyl; or
a pharmaceutically acceptable salt or ester thereof.

13. The compound according to claim 1 wherein R¹¹ is chlorophenyl or fluorophenyl.

14. The compound according to claim 1 wherein R¹² is phenyl or bromophenyl.

15. The compound according to claim 1, wherein R¹³ is halogen, haloalkoxy or alkoxyalkoxy.

16. The compound according to claim 1 wherein:
R¹¹ is chlorophenyl or fluorophenyl;
R¹² is phenyl or bromophenyl;
R¹³ is halogen, haloalkoxy or alkoxyalkoxy; or,
a pharmaceutically acceptable salt or ester thereof.

17. The compound according to claim 1 wherein R¹³ is chloro, trifluoromethoxy or methoxyethoxy.

18. The compound according to claim 1 wherein R¹⁴ is halogen.

19. The compound according to claim 1 wherein R¹⁴ is chloro.

20. The compound according claim 1, wherein R¹⁵ is hydrogen.

21. The compound according to claim 16 wherein:
R¹³ is chloro, trifluoromethoxy or methoxyethoxy;
R¹⁴ is chloro;
R¹⁵ is hydrogen; or
a pharmaceutically acceptable salt or ester thereof.

22. The compound according to claim 1 which compound is selected from the group consisting of;
(S)—N-(3-(3-chloro-4-(trifluoromethoxy)phenyl)-1-(1-cyanocyclopropylamino)-1-oxopropan-2-yl)-1-(2,2-difluoroethyl)-3-(trifluoromethyl)-1H-pyrazole-5-carboxamide;
(S)—N-(3-(3-chloro-4-(trifluoromethoxy)phenyl)-1-(1-cyanocyclopropylamino)-1-oxopropan-2-yl)-1-methyl-3-(trifluoromethyl)-1H-pyrazole-5-carboxamide;
(S)—N-(3-(3-chloro-4-(trifluoromethoxy)phenyl)-1-(1-cyanocyclopropylamino)-1-oxopropan-2-yl)-1,3-dimethyl-1H-pyrazole-5-carboxamide;
(S)—N-(3-(3-chloro-4-(trifluoromethoxy)phenyl)-1-(1-cyanocyclopropylamino)-1-oxopropan-2-yl)-3-cyclopropyl-1-methyl-1H-pyrazole-5-carboxamide;
(S)-3-tert-butyl-N-(3-(3-chloro-4-(trifluoromethoxy)phenyl)-1-(1-cyanocyclopropylamino)-1-oxopropan-2-yl)-1-methyl-1H-pyrazole-5-carboxamide;
(S)—N-(3-(3-chloro-4-(trifluoromethoxy)phenyl)-1-(1-cyanocyclopropylamino)-1-oxopropan-2-yl)-1-(4-fluorophenyl)-1H-pyrazole-3-carboxamide;
(S)—N-(3-(3-chloro-4-(trifluoromethoxy)phenyl)-1-(1-cyanocyclopropylamino)-1-oxopropan-2-yl)-1-methyl-3-phenyl-1H-pyrazole-5-carboxamide;
(S)—N-(3-(3-chloro-4-(trifluoromethoxy)phenyl)-1-(1-cyanocyclopropylamino)-1-oxopropan-2-yl)-2-(4-chlorophenyl)-5-methyloxazole-4-carboxamide;
(S)—N-(3-(3-chloro-4-(trifluoromethoxy)phenyl)-1-(1-cyanocyclopropylamino)-1-oxopropan-2-yl)-2-(4-fluorophenyl)-2H-1,2,3-triazole-4-carboxamide;
(S)—N-(3-(3-chloro-4-(trifluoromethoxy)phenyl)-1-(1-cyanocyclopropylamino)-1-oxopropan-2-yl)-3-(2-chlorophenyl)-1H-pyrazole-5-carboxamide;
(S)—N-(3-(3-chloro-4-(trifluoromethoxy)phenyl)-1-(1-cyanocyclopropylamino)-1-oxopropan-2-yl)-3-(4-fluorophenyl)-1H-pyrazole-5-carboxamide;
(S)—N-(3-(3-chloro-4-(trifluoromethoxy)phenyl)-1-(1-cyanocyclopropylamino)-1-oxopropan-2-yl)-3-(4-methoxyphenyl)-1H-pyrazole-5-carboxamide,
(S)—N-(3-(3-chloro-4-(trifluoromethoxy)phenyl)-1-(1-cyanocyclopropylamino)-1-oxopropan-2-yl)-3-phenylisoxazole-5-carboxamide;
(S)—N-(3-(3-chloro-4-(trifluoromethoxy)phenyl)-1-(1-cyanocyclopropylamino)-1-oxopropan-2-yl)-5-(3-fluorophenyl)-1,2,4-oxadiazole-3-carboxamide;
(S)—N-(3-(3-chloro-4-(trifluoromethoxy)phenyl)-1-(1-cyanocyclopropylamino)-1-oxopropan-2-yl)-2-phenyl-2H-1,2,3-triazole-4-carboxamide;
(S)—N-(3-(3-chloro-4-(trifluoromethoxy)phenyl)-1-(1-cyanocyclopropylamino)-1-oxopropan-2-yl)-3-(3-chlorophenyl)-1-methyl-1H-pyrazole-5-carboxamide;
(S)—N-(3-(3-chloro-4-(trifluoromethoxy)phenyl)-1-(1-cyanocyclopropylamino)-1-oxopropan-2-yl)-5-(3-chlorophenyl)-1,2,4-oxadiazole-3-carboxamide;
(2S)-2-(1-(5-(4-bromophenyl)-1,3,4-oxadiazol-2-yl)-2,2,2-trifluoroethylamino)-3-(3-chloro-4-(trifluoromethoxy)phenyl)-N-(1-cyanocyclopropyl)propanamide;

(2S)-3-(3-chloro-4-(trifluoromethoxy)phenyl)-N-(1-cyanocyclopropyl)-2-(2,2,2-trifluoro-1-(5-phenyl-1,3,4-oxadiazol-2-yl)ethylamino)propanamide;
N-[(2S)-3-[3-chloro-4-(trifluoromethoxy)phenyl]-1-[(1-cyanocyclopropyl)amino]-1-oxopropan-2-yl]-2-(4-methylsulfanylphenyl)triazole-4-carboxamide;
2-(4-chlorophenyl)-N-[(2S)-3-[3-chloro-4-(trifluoromethoxy)phenyl]-1-[(1-cyanocyclopropyl)amino]-1-oxopropan-2-yl]triazole-4-carboxamide;
N-[(2S)-3-(3-chlorophenyl)-1-[(1-cyanocyclopropyl)amino]-1-oxopropan-2-yl]-2-(4-fluorophenyl)triazole-4-carboxamide;
N-[(2S)-3-[3-chloro-4-(trifluoromethoxy)phenyl]-1-[(1-cyanocyclopropyl)amino]-1-oxopropan-2-yl]-2-pyridin-3-yltriazole-4-carboxamide;
N-[(2S)-1-[(1-cyanocyclopropyl)amino]-1-oxo-3-phenylpropan-2-yl]-2-(4-fluorophenyl)triazole-4-carboxamide;
N-[(2S)-3-[3-chloro-4-(cyclopropylmethoxy)phenyl]-1-[(1-cyanocyclopropyl)amino]-1-oxopropan-2-yl]-2-(4-fluorophenyl)triazole-4-carboxamide;
N-[(2S)-1-[(1-cyanocyclopropyl)amino]-3-(3,4-dichlorophenyl)-1-oxopropan-2-yl]-2-(4-fluorophenyl)triazole-4-carboxamide;
N-[(2S)-3-[3-chloro-4-(trifluoromethoxy)phenyl]-1-[(1-cyanocyclopropyl)amino]-1-oxopropan-2-yl]-2-(6-fluoropyridin-3-yl)triazole-4-carboxamide;
N-[(2S)-1-[(1-cyanocyclopropyl)amino]-1-oxo-3-(4-phenylmethoxyphenyl)propan-2-yl]-2-(4-fluorophenyl)triazole-4-carboxamide;
N-[(2S)-1-[(1-cyanocyclopropyl)amino]-4-methyl-1-oxopentan-2-yl]-2-(4-fluorophenyl)triazole-4-carboxamide;
N-[(2S)-3-[3-chloro-4-(trifluoromethoxy)phenyl]-1-[(1-cyanocyclopropyl)amino]-1-oxopropan-2-yl]-2-propan-2-yltriazole-4-carboxamide;
N-[(2S)-3-[3-chloro-4-(trifluoromethoxy)phenyl]-1-[(1-cyanocyclopropyl)amino]-1-oxopropan-2-yl]-2-methyltriazole-4-carboxamide;
2-(4-bromophenyl)-N-[(2S)-3-[3-chloro-4-(trifluoromethoxy)phenyl]-1-[(1-cyanocyclopropyl)amino]-1-oxopropan-2-yl]triazole-4-carboxamide;
N-[(2S)-3-[3-chloro-4-(2-methoxyethoxy)phenyl]-1-[(1-cyanocyclopropyl)amino]-1-oxopropan-2-yl]-2-(4-fluorophenyl)triazole-4-carboxamide;
2-tert-butyl-N-[(2S)-3-[3-chloro-4-(trifluoromethoxy)phenyl]-1-[(1-cyanocyclopropyl)amino]-1-oxopropan-2-yl]triazole-4-carboxamide;
N-[(2S)-3-[3-chloro-4-(cyclobutylmethoxy)phenyl]-1-[(1-cyanocyclopropyl)amino]-1-oxopropan-2-yl]-2-(4-fluorophenyl)triazole-4-carboxamide;
N-[(2S)-1-[(1-cyanocyclopropyl)amino]-1-oxo-3-pyridin-4-ylpropan-2-yl]-2-(4-fluorophenyl)triazole-4-carboxamide;
N-[(2S)-3-(4-chlorophenyl)-1-[(1-cyanocyclopropyl)amino]-1-oxopropan-2-yl]-2-(4-fluorophenyl)triazole-4-carboxamide;
N-[(2S)-3-[3-chloro-4-(trifluoromethoxy)phenyl]-1-[(1-cyanocyclopropyl)amino]-1-oxopropan-2-yl]-2-pyridin-4-yltriazole-4-carboxamide;
N-[(2S)-3-[3-chloro-4-(trifluoromethoxy)phenyl]-1-[(1-cyanocyclopropyl)amino]-1-oxopropan-2-yl]-2-cyclobutyltriazole-4-carboxamide;
N-[(2S)-3-(3-chloro-4-cyanophenyl)-1-[(1-cyanocyclopropyl)amino]-1-oxopropan-2-yl]-2-(4-fluorophenyl)triazole-4-carboxamide;
N-[(2S)-3-[3-chloro-4-(trifluoromethoxy)phenyl]-1-[(1-cyanocyclopropyl)amino]-1-oxopropan-2-yl]-2-(oxan-4-yl)triazole-4-carboxamide;
N-[(2S)-1-[(1-cyanocyclopropyl)amino]-3-(3,4-dichlorophenyl)-1-oxopropan-2-yl]-2-(oxan-4-yl)triazole-4-carboxamide;
N-[(2S)-3-[3-chloro-4-(trifluoromethoxy)phenyl]-1-[(1-cyanocyclopropyl)amino]-1-oxopropan-2-yl]-2-cyclohexyltriazole-4-carboxamide;
N-[(2S)-1-[(1-cyanocyclopropyl)amino]-3-(2-cyanophenyl)-1-oxopropan-2-yl]-2-(4-fluorophenyl)triazole-4-carboxamide;
N-[(2S)-1-[(1-cyanocyclopropyl)amino]-1-oxo-3-[2-(trifluoromethyl)phenyl]propan-2-yl]-2-(4-fluorophenyl)triazole-4-carboxamide;
N-[(2S)-3-(2-chlorophenyl)-1-[(1-cyanocyclopropyl)amino]-1-oxopropan-2-yl]-2-(4-fluorophenyl)triazole-4-carboxamide;
N-[(2S)-1-[(1-cyanocyclopropyl)amino]-3-(3,4-dichlorophenyl)-1-oxopropan-2-yl]-2-(3,3-difluorocyclobutyl)triazole-4-carboxamide;
tert-butyl 6-[4-[[(2S)-3-[3-chloro-4-(trifluoromethoxy)phenyl]-1-[(1-cyanocyclopropyl)amino]-1-oxopropan-2-yl]carbamoyl]triazol-2-yl]-2-azaspiro[3.3]heptane-2-carboxylate;
N-[(2S)-1-[(1-cyanocyclopropyl)amino]-3-(3,4-dichlorophenyl)-1-oxopropan-2-yl]-2-cyclobutyltriazole-4-carboxamide;
N-[(2S)-3-[3-chloro-4-(trifluoromethoxy)phenyl]-1-[(1-cyanocyclopropyl)amino]-1-oxopropan-2-yl]-2-(3,3-difluorocyclobutyl)triazole-4-carboxamide;
N-[(2S)-1-[(1-cyanocyclopropyl)amino]-3-(3,4-dichlorophenyl)-1-oxopropan-2-yl]-2-(oxetan-3-yl)triazole-4-carboxamide;
N-[(2S)-3-[3-chloro-4-(trifluoromethoxy)phenyl]-1-[(1-cyanocyclopropyl)amino]-1-oxopropan-2-yl]-2-(oxetan-3-yl)triazole-4-carboxamide;
2-(2-azaspiro[3.3]heptan-6-yl)-N-[(2S)-3-[3-chloro-4-(trifluoromethoxy)phenyl]-1-[(1-cyanocyclopropyl)amino]-1-oxopropan-2-yl]triazole-4-carboxamide;
tert-butyl 3-[4-[[(2S)-3-[3-chloro-4-(trifluoromethoxy)phenyl]-1-[(1-cyanocyclopropyl)amino]-1-oxopropan-2-yl]carbamoyl]triazol-2-yl]pyrrolidine-1-carboxylate;
N-[(2S)-3-[3-chloro-4-(trifluoromethoxy)phenyl]-1-[(1-cyanocyclopropyl)amino]-1-oxopropan-2-yl]-2-pyrrolidin-3-yltriazole-4-carboxamide;
2-(azetidin-3-yl)-N-[(2S)-3-[3-chloro-4-(trifluoromethoxy)phenyl]-1-[(1-cyanocyclopropyl)amino]-1-oxopropan-2-yl]triazole-4-carboxamide; and
N-[(2S)-1-[(1-cyanocyclopropyl)amino]-1-oxo-3-pyridin-2-ylpropan-2-yl]-2-(4-fluorophenyl)triazole-4-carboxamide; or
a pharmaceutically acceptable salt thereof.

23. The compound according to claim 1 which compound is selected from the group consisting of:
(S)—N-(3-(3-chloro-4-(trifluoromethoxy)phenyl)-1-(1-cyanocyclopropylamino)-1-oxopropan-2-yl)-2-(4-fluorophenyl)-2H-1,2,3-triazole-4-carboxamide;
(S)—N-(3-(3-chloro-4-(trifluoromethoxy)phenyl)-1-(1-cyanocyclopropylamino)-1-oxopropan-2-yl)-3-phenylisoxazole-5-carboxamide;
(S)—N-(3-(3-chloro-4-(trifluoromethoxy)phenyl)-1-(1-cyanocyclopropylamino)-1-oxopropan-2-yl)-2-phenyl-2H-1,2,3-triazole-4-carboxamide;
2-(4-chlorophenyl)-N-[(2S)-3-[3-chloro-4-(trifluoromethoxy)phenyl]-1-[(1-cyanocyclopropyl)amino]-1-oxopropan-2-yl]triazole-4-carboxamide;

N-[(2S)-3-[3-chloro-4-(trifluoromethoxy)phenyl]-1-[(1-cyanocyclopropyl)amino]-1-oxopropan-2-yl]-2-pyridin-3-yltriazole-4-carboxamide;

N-[(2S)-1-[(1-cyanocyclopropyl)amino]-3-(3,4-dichlorophenyl)-1-oxopropan-2-yl]-2-(4-fluorophenyl)triazole-4-carboxamide;

N-[(2S)-3-[3-chloro-4-(trifluoromethoxy)phenyl]-1-[(1-cyanocyclopropyl)amino]-1-oxopropan-2-yl]-2-(6-fluoropyridin-3-yl)triazole-4-carboxamide;

N-[(2S)-3-[3-chloro-4-(trifluoromethoxy)phenyl]-1-[(1-cyanocyclopropyl)amino]-1-oxopropan-2-yl]-2-propan-2-yltriazole-4-carboxamide;

N-[(2S)-3-[3-chloro-4-(trifluoromethoxy)phenyl]-1-[(1-cyanocyclopropyl)amino]-1-oxopropan-2-yl]-2-methyltriazole-4-carboxamide;

N-[(2S)-3-[3-chloro-4-(2-methoxyethoxy)phenyl]-1-[(1-cyanocyclopropyl)amino]-1-oxopropan-2-yl]-2-(4-fluorophenyl)triazole-4-carboxamide; and 2-tert-butyl-N-[(2S)-3-[3-chloro-4-(trifluoromethoxy)phenyl]-1-[(1-cyanocyclopropyl)amino]-1-oxopropan-2-yl]triazole-4-carboxamide; or, a pharmaceutically acceptable salt thereof.

24. A process for the manufacture of a compound according to claim 1 comprising the reaction of a compound of formula (A)

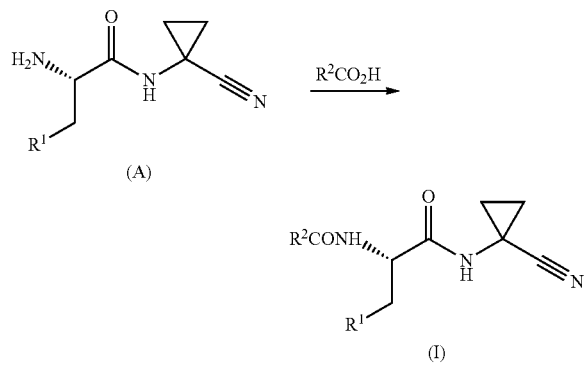

with a compound of formula $R^2COOH$, a coupling agent and a base to afford a compound of formula I.

25. A process for the manufacture of a compound according to claim 1 comprising the reaction of a compound of formula (A)

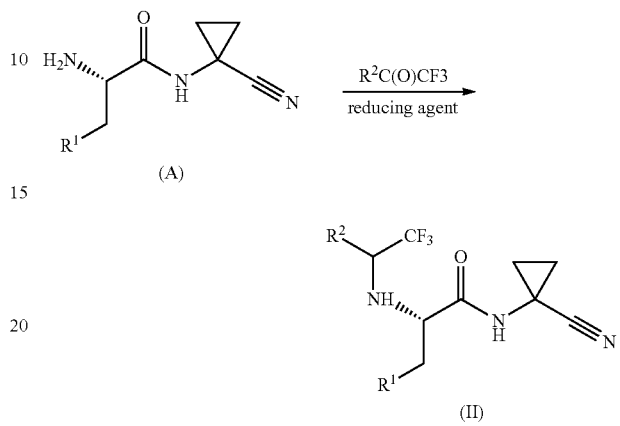

as defined above in the presence of $R^2C(O)CF_3$ and a reducing agent to afford a compound of formula II.

26. A pharmaceutical composition comprising a compound of claim 1 and a at least one pharmaceutically acceptable carrier, excipient or therapeutically inert carrier, excipient or diluent.

27. A method for the treatment of Human African Trypanosomiasis or African Sleeping Sickness, which method comprises administering a therapeutically effective of a compound as defined in claim 1 to a patient in need thereof.

28. The compound (S)—N-(3-(3-chloro-4-(trifluoromethoxy)phenyl)-1-(1-cyanocyclopropylamino)-1-oxopropan-2-yl)-5-methyl-2-phenyl-2H-1,2,3-triazole-4-carboxamide.

* * * * *